(12) United States Patent
Sirkar

(10) Patent No.: US 12,239,943 B2
(45) Date of Patent: Mar. 4, 2025

(54) CONTINUOUS PRODUCTION OF ACTIVE PHARMACEUTICAL INGREDIENTS

(71) Applicant: New Jersey Institute of Technology, Newark, NJ (US)

(72) Inventor: Kamalesh Sirkar, Bridgewater, NJ (US)

(73) Assignee: New Jersey Institute of Technology, Newark, NJ (US)

( * ) Notice: Subject to any disclaimer, the term of this patent is extended or adjusted under 35 U.S.C. 154(b) by 17 days.

(21) Appl. No.: 18/241,405

(22) Filed: Sep. 1, 2023

(65) Prior Publication Data

US 2023/0405488 A1 Dec. 21, 2023

Related U.S. Application Data

(62) Division of application No. 17/546,305, filed on Dec. 9, 2021, now Pat. No. 11,779,859.

(60) Provisional application No. 63/123,172, filed on Dec. 9, 2020.

(51) Int. Cl.
| | |
|---|---|
| C07C 213/06 | (2006.01) |
| B01D 9/00 | (2006.01) |
| B01D 9/02 | (2006.01) |
| B01D 11/04 | (2006.01) |
| B01D 61/28 | (2006.01) |
| B01D 61/36 | (2006.01) |
| B01D 63/02 | (2006.01) |
| C07C 213/10 | (2006.01) |
| C07D 403/06 | (2006.01) |

(52) U.S. Cl.
CPC .............. *B01D 9/0059* (2013.01); *B01D 9/02* (2013.01); *B01D 11/0492* (2013.01); *B01D 61/28* (2013.01); *B01D 61/362* (2013.01); *B01D 63/02* (2013.01); *C07C 213/06* (2013.01); *C07C 213/10* (2013.01); *C07D 403/06* (2013.01); *B01D 2009/0086* (2013.01)

(58) Field of Classification Search
None
See application file for complete search history.

(56) References Cited

U.S. PATENT DOCUMENTS

| 9,085,476 B2 | 7/2015 | Sirkar |
| 11,779,859 B2 | 10/2023 | Sirkar |
| 2002/0176321 A1 | 11/2002 | Knight |

OTHER PUBLICATIONS

Korotney, Water Phase Separation in Oxygenated Gasoline, Memorandum, pp. 1-6, 1995.

(Continued)

*Primary Examiner* — Sudhakar Katakam
*Assistant Examiner* — Jennifer C Sawyer
(74) *Attorney, Agent, or Firm* — McCarter & English, LLP

(57) ABSTRACT

The present invention is directed to a method of producing active pharmaceutical ingredients (APIs). The method includes subjecting a reaction mixture with an API precursor to solvent extraction to produce a reactant stream with the API precursor. The method includes concentrating the API precursor in the reactant stream using at least one membrane. The method includes carrying out a reaction in a membrane reactor. The method includes separating the API precursor from the reaction stream using a separator. The method includes crystallizing the API precursor using a crystallizer to produce APIs.

15 Claims, 14 Drawing Sheets

(56) References Cited

OTHER PUBLICATIONS

Nidetzky, et al., Continuous Enzymatic Production of Xylitol with Simultaneous Coenzyme Regeneration in a Charged Membrane Reactor, Biotechnol. Bioeng., 52, 387-396, 1996.

Lopez, et al., A Multiphase/Extractive Enzyme Membrane Reactor for Production of Diltiazem Chiral Intermediate, Journal of Membrane Science, 125, pp. 189-211, 1997.

Shanbhag, et al., Membrane-Based Ozonation of Organic Compounds, Ind. Eng. Chem. Res., 37, 4388-4398, 1998.

Sirkar, et al., Membrane in a Reactor: A Functional Perspective, Ind. Eng. Chem. Res., 38, 3715-3737, 1999.

Whu, et al., Modeling of Nanofiltration-Assisted Organic Synthesis, J. Membrane Science, 163(12), 319-331, 1999.

Joscelyne, et al., Membrane Emulsification—A Literature Review, Journal of Membrane Science, 169, 107-117, 2000.

Lim, et al., Design Issues of Pervaporation Membrane Reactors for Esterification, Chem. Eng. Sci., 57, 4933-4946, 2002.

Luthra, et al., Homogeneous Phase Transfer Catalyst Recovery and Re-Use Using Solvent Resistant Membranes, Journal of Membrane Science, 201, 65-75, 2002.

Scarpello, et al., The Separation of Homogeneous Organometallic Catalysts Using Solvent Resistant Nanofiltration, Journal of Membrane Science, 203, 71-85, 2002.

Sheth, et al., Nanofiltration-Based Diafiltration Process for Solvent Exchange in Pharmaceutical Manufacturing, Journal of Membrane Science, 211, 251-261, 2003.

Tharwat, et al., Formation and Stability of Nano-Emulsions, Advances in Colloid and Interface Science, 2004. 9: p. 108-109.

Zarkadas, et al., Polymeric Hollow Fiber Heat Exchangers: An Alternative for Lower Temperature Applications, Ind. Eng. Chem. Res., 43, 8093-8106, 2004.

Zarkadas, et al., Solid Hollow Fiber Cooling Crystallization, Ind. Eng. Chem. Res., 43, 7163-7180, 2004.

Wong, et al., Recovery and Reuse of Ionic Liquids and Palladium Catalyst for Suzuki Reactions Using Organic Solvent Nanofiltration, Green Chem., 8, 373-399, 2006.

Zarkadas, et al., Antisolvent Crystallization in Porous Hollow Fiber Devices, Chemical Engineering Science, 61, 5030-5048, 2006.

Hu, et al., Influence of Membrane Material and Corrugation and Process Conditions on Emulsion Microfiltration. Journal of Membrane Science, 2007, 294 (1-2): p. 30-39.

Sirkar, Membranes, Phase Interfaces, and Separations: Novel Techniques and Membranes—An Overview, Ind. Eng. Chem. Res., 47, 5250-5266, 2008.

Song, et al., Pilot Plant Studies of Novel Membranes and Devices for Direct Contact Membrane Distillation-Based Desalination, Journal of Membrane Science, 323, 257-270, 2008.

Song, et al., Polymeric Hollow-Fiber Heat Exchangers for Thermal Desalination Processes, Ind. Eng. Chem. Res., 49, 11961-11977, 2010.

LaPorte, et al., Process Development and Case Studies of Continuous Reactor Systems for Production of API and Pharmaceutical Intermediates, Chapter 23, pp. 437-455, in Am Ende, D. (ED.), "Chemical Engineering in the Pharmaceutical Industry: R&D to Manufacturing", John Wiley & Sons, Hoboken, NJ, 2011.

Lu, et al., Hyperlenses and Metalenses for Far-Field Super-Resolution Imaging, Nature communications, 2012, 3(1): p. 1-9.

Tang et al., Perfluoropolymer Membrane Behaves Like a Zeolite Membrane in Dehydration of Aprotic Solvents, Journal of Membrane Science, 421-422, pp. 211-216, 2012.

Singh, et al., From Protein Engineering to Immobilization: Promising Strategies for the Upgrade of Industrial Enzymes, Int. J. Mol. Sci., 14(1), 1232-1277, 2013.

Tang, et al., Permeation and Sorption of Organic Solvents and Separation of Their Mixtures Through an Amorphous Perfluoropolymer Membrane in Pervaporation, Journal of Membrane Science, 447, 345-354, 2013.

Chen, et al., Continuous Polymer Nanocoating on Silica Nanoparticles, Langmuir, 30, 7804-7810, 2014.

Marchetti, et al., Molecular Separation with Organic Solvent Nanofiltration: A Critical Review, Chemical Reviews, 114, 10735-10806, 2014.

Singh, et al., High Temperature Direct Contact Membrane Distillation Based Desalination Using PTFE Hollow Fibers, Chemical Engineering Science, 116, 824-833, 2014.

Chen, et al., Continuous Synthesis of Polymer-Coated Drug Particles by Porous Hollow Fiber Membrane-Based Antisolvent Crystallization, Langmuir, 31, 432-441, 2015.

Adamo, et al., On-Demand Continuous-Flow Production of Pharmaceuticals in a Compact, Reconfigurable System, Research, vol. 352, Issue 6281, 2016.

Chen, et al., Continuous Preparation of Polymer Coated Drug Crystals by Solid Hollow Fiber Membrane-Based Cooling Crystallization, International Journal of Pharmaceutics, 499, 395-402, 2016.

Motamedhashemi, et al., Flow-Through Catalytic Membrane Reactors for the Destruction of a Chemical Warfare Simulant: Dynamic Performance Aspects, Catalysis Today, 268, 130-141, 2016.

Peer, et al., Biphasic Catalytic Hydrogen Peroxide Oxidation of Alcohols in Flow: Scale-Up and Extraction, Org. Process Res. Dev., 20, 1677-1685, 2016.

Cole, et al., Kilogram-Scale Prexasertib Monolactate Monohydrate Synthesis Under Continuous-Flow GGMP Conditions, Research, Science, 356, 1144-1150, 2017.

Li, et al., Desalination Performances of Large Hollow Fiber-Based DCMD Devices, L&EC Research, Ind. Eng. Chem. Res., 56, 1594-1603, 2017.

Chau, et al., Reverse Osmosis Separation of Particular Organic Solvent Mixtures by a Perfluorodioxole Copolymer Membrane, Journal of Membrane Science, 563, 541-551, 2018.

Chen, et al., Hydrodynamic Modeling of Porous Hollow Fiber Anti-Solvent Crystallizer for Continuous Production of Drug Crystals, Journal of Membrane Science, 556, 185-195, 2018.

Fern, et al., Continuous Synthesis of Nano-Drug Particles by Antisolvent Crystallization Using a Porous Hollow-Fiber Membrane Module, International Journal of Pharmaceutics, 543, 139-150, 2018.

Kuehn, Pharmaceutical Manufacturing: Current Trends and What's Next, American Institute of Chemical Engineers, CEP, pp. 23-29, 2018.

Li, et al., Continuous Production of Anhydrous tert-Butyl Hydroperoxide in Nonane Using Membrane Pervaporation and Its Application in Flow Oxidation of a y-Butyrolactam, Org. Process Res. Dev., 22, 707-720, 2018.

Singh, et al., Novel Cylindrical Cross-Flow Hollow Fiber Membrane Module for Direct Contact Membrane Distillation-Based Desalination, Journal of Membrane Science, 545, 312-322, 2018.

Zhou, et al., Continuous Production of Drug Nanocrystals by Porous Hollow Fiber-Based Anti-Solvent Crystallization, Journal of Membrane Science, 564, 682-690, 2018.

Cho, et al., Site-Selective Enzymatic C—H Amidation for Synthesis of Diverse Lactams, Science, 364, 6440, 575-578, 2019.

Liu, et al. A Molecular Simulation Protocol for Swelling and Organic Solvent Nanofiltration of Polymer Membranes, Journal of Membrane Science, 573, 639-646, 2019.

CONTINUOUS PRODUCTION OF ACTIVE PHARMACEUTICAL INGREDIENTS

CROSS-REFERENCE TO RELATED APPLICATIONS

This application claims the benefit of co-pending U.S. Non-Provisional patent application Ser. No. 17/546,305, which was filed on Dec. 9, 2021, and which claimed priority benefit to Provisional Patent Application No. 63/123,172, which was filed on Dec. 9, 2020. The entire contents of the foregoing non-provisional and provisional patent applications are is incorporated herein by reference.

BACKGROUND

Active pharmaceutical ingredients (APIs) are traditionally produced by batch chemical synthesis processes. Some APIs are beginning to be produced by continuous manufacturing. Batch chemical synthesis processes may involve a large number of synthesis steps (e.g., as many as 20 synthesis steps). Such batch processes can involve large batch volumes and considerable hold time between steps. In some instances, a large amount of product loss may occur if the quality of the resulting product is affected during the processing steps. Continuous manufacturing methods generally involve a number of synthesis steps. (See, e.g., Kuehn, S., Pharmaceutical manufacturing: Current trends and what's next, CEP, p. 23-29, December 2018). The volume of material moving through a continuous manufacturing process is generally quite small (as compared to batch chemical synthesis processes) and the quality of the resulting product can be monitored on a continuous basis during the process.

FIG. 1 is a schematic of an exemplary traditional continuous pharmaceutical production sequence of reactors and separators. In particular, FIG. 1 illustrates one traditional multistep continuous API synthesis process. The process or sequence illustrated in FIG. 1 can be performed by a system 10 including a mixer 12, a first reactor 14, a first heat exchanger 16, a first solvent separator 18, a second reactor 20, a second heat exchanger 22, a second solvent separator 24, and a crystallizer 26. The system 10 can include a number of such sequences depending on the number of reaction/synthesis steps of the process. Each synthesis step in API manufacturing essentially includes a reaction step followed by work-up such that the next synthesis step can be implemented. The process continues with a number of consecutive reaction steps followed ultimately by isolation and purification. Generally, crystallization is the process used for purification, followed by various steps for oral dosage-form manufacturing. The chemical synthesis reaction step in a reactor may be preceded by mixing and is generally followed by a separator, filter and/or an evaporator/distillation device. In addition, there may be heating or cooling before, during, and/or after the synthesis step in the reactor.

Some traditional continuous manufacturing sequences using traditional devices have been used to synthesize four APIs: diphenhydramine hydrochloride (BENADRYL®), lidocaine hydrochloride, diazepam (VALIUM®), and fluoxetine hydrochloride. (See, e.g., Adamo, A. et al., On-demand continuous-flow production of pharmaceuticals in a compact, reconfigurable system, Science, vol. 352, 6281, 61-67 (2016)). The unit operation and unit process steps/devices repeatedly used in such traditional continuous manufacturing sequences are: a reactor, a packed-bed column-based solvent extractor, a gravity-based liquid-liquid separator, a filter, a reagent/solvent delivery and mixing, a heater, a charcoal cartridge for adsorption, a precipitation/crystallization device, and an occasional membrane separator. See id.

FIG. 2 is a flowchart showing the upstream and downstream synthesis of diphenhydramine hydrochloride (BENADRYL®) using a traditional reconfigurable system 30. (See, e.g., Adamo, A. et al., On-demand continuous-flow production of pharmaceuticals in a compact, reconfigurable system, Science, vol. 352, 6281, 61-67 (2016)). The components of the system 30 include a 10 mL reactor 32, a back-pressure regulator 34, a heater 36, a packed-bed column 38, a gravity-based separator 40, a charcoal cartridge 44, and a Fourier Transform Infrared Spectroscopy instrument 46 (FlowIR). After addition of HCl, the API precipitates and is filtered (filter not shown in FIG. 2).

FIG. 3A is a flowchart showing the synthesis of lidocaine hydrochloride using a two-step upstream system 50 configuration. (See, e.g., Adamo, A. et al., On-demand continuous-flow production of pharmaceuticals in a compact, reconfigurable system, Science, vol. 352, 6281, 61-67 (2016)). The system 50 includes a 10 mL reactor 52, a 30 mL reactor 54, a back-pressure regulator 56, a packed-bed column-based solvent extractor 58, a gravity-based separator 60, and a FlowIR 64.

FIG. 3B is a flowchart showing the synthesis of diazepam (VALIUM®) using a two-step upstream system 70 configuration. The system 70 includes two 10 mL reactors 72, 74, a back-pressure regulator 76, a packed-bed column 78, gravity-based separators 80, 86, a charcoal cartridge 82, and a FlowIR 84.

As shown from FIGS. 1, 2 and 3A-3B, there is currently an interest in manufacturing APIs using a continuous manufacturing process. However, traditional continuous production processes may result in low efficiency, operational problems, reduced or lack of control over production, combinations thereof, or the like. Accordingly, there is a need for an improved continuous process for production of APIs.

SUMMARY

The present invention relates to a method to continuously produce APIs including the use of membrane-based devices. In some embodiments, membrane-based devices can be incorporated at one or more steps of the API manufacturing process. In some embodiments, membrane-based devices can be incorporated at every step of the API manufacturing process. The molecular weights of the APIs can be in the range of, e.g., 150-1100 Da inclusive, 150-1000 Da inclusive, 150-900 Da inclusive, 150-800 Da inclusive, 150-700 Da inclusive, 150-600 Da inclusive, 150-500 Da inclusive, 150-400 Da inclusive, 150-300 Da inclusive, 150-200 Da inclusive, 200-1100 Da inclusive, 300-1100 Da inclusive, 400-1100 Da inclusive, 500-1100 Da inclusive, 600-1100 Da inclusive, 700-1100 Da inclusive, 800-1100 Da inclusive, 900-1100 Da inclusive, 1000-1100 Da inclusive, 200-1000 Da inclusive, 300-900 Da inclusive, 400-800 Da inclusive, 500-700 Da inclusive, 150 Da, 200 Da, 300 Da, 400 Da, 500 Da, 600 Da, 700 Da, 800 Da, 900 Da, 1000 Da, 1100 Da, or the like. In some embodiments, other molecular weights can be used.

In some embodiments, the exemplary method to produce APIs can include several steps. Initially, a reaction mixture with an API precursor is subjected to solvent extraction to produce a reactant stream with the API precursor. The API precursor is concentrated in the reactant stream using at least one membrane. The API precursor undergoes conversion in the reactor and is then separated from the reaction mixture stream using a separator. The converted API precursor is then crystallized using a crystallizer to produce APIs. Before and after the reaction step, the API precursor and the converted API precursor in solution may undergo heating or cooling.

The exemplary method incorporates membrane devices and processes. In contrast to traditional methods, such as batch manufacturing and continuous processes using non-membrane devices and processes, membrane technologies are compact, modular, scalable, and highly energy efficient. Membrane technologies are also capable of many separations in a continuous fashion. Membrane reactors can reach a higher level of synthesis than the tubular reactors traditionally used for API production. Generally, flow chemistry-based approaches use simple channel/tubular flows and can encounter severe additional challenges with multiphasic systems (gas-liquid, liquid-liquid, solid-liquid, or solid-liquid-gas). Membrane crystallizers, membrane mixers, and solid hollow fiber and ceramic tubular exchangers can carry out the process of crystallization, mixing, and/or heat exchange, respectively, much more efficiently than conventional non-membrane based devices.

In some embodiments, every unit (or virtually every unit) used in API manufacturing can be a membrane device. In such embodiments, all units can be connected in a serial fashion and operate continuously to enable continuous membrane-based production of APIs (without batch processing).

In general, a central component of an API production system includes reactors for synthesis of pharmaceutical intermediates and the API. API synthesis can involve a number of reaction steps, e.g., from 2, 3, 4 to 20 reaction steps, or more. In the exemplary method, each reaction step can be carried out in a membrane reactor in a continuous fashion. Steps related to any reaction carried out before introduction to the reactor (such as mixing reactants, heating the feed, or the like) or after the reaction (such as quenching the post-reaction mixture or cooling) can be carried out using membrane-based devices. In some embodiments, the membrane reactor itself can carry out additional functions, such as feed mixture separation or product mixture separation.

In some embodiments, after each reaction, membrane separation steps can be coupled with the membrane reactor output and separations/purifications of the intermediates/API can be carried out. In some embodiments, membrane reactors can be used at every synthesis step, with the membrane reactors supported by membrane separations at each post-reaction processing step. All of the noted steps can be carried out continuously to continuously manufacture APIs.

In some aspects, the present invention relates to a method of producing active pharmaceutical ingredients (APIs), including: (a) subjecting a reaction mixture with an API precursor to solvent extraction to produce a reactant stream with the API precursor; (b) concentrating the API precursor in the reactant stream using at least one membrane; (c) carrying out a reaction in a membrane reactor; (d) separating the API precursor from the reaction stream using a separator; and crystallizing the API precursor using a crystallizer to produce APIs.

In some embodiments, at least one of a reactor for performing step (a), the separator of step (d), or the crystallizer of step (e) is a membrane-based device. In some embodiments, the method of producing APIs includes heating, cooling, and/or quenching of solutions containing active pharmaceutical ingredients using solid hollow fiber heat exchangers. In further embodiments, the heat exchangers are membrane-based. In some embodiments, the method of producing APIs includes removing impurities from organic process streams using membrane adsorbers.

In some aspects, the present invention relates to a method for solvent exchange and nanofiltration or reverse osmosis, including: (a) adding a solvent to a reaction mixture; and (b) removing preexisting solvent from the reaction mixture through a membrane by organic solvent nanofiltration or organic solvent reverse osmosis.

In some aspects, the present invention relates to a method to immobilize catalysts in pores of polymeric or ceramic planar, tubular or hollow fiber membranes for carrying out two-phase based reactions in this membrane reactor for gas-liquid systems as well as liquid-liquid systems.

In some aspects, the present invention relates to a method to immobilize a catalyst using membrane-based devices in enzyme catalysis, including: (a) directing a reaction mixture containing small molecule substrates and products through a membrane reactor lined with charged nanofiltration membranes; and (b) segregating a catalyst and cofactor in the reactor and immobilizing the catalyst in a membrane.

In some aspects, the present invention relates to a method for continuous manufacturing of prexasertib monolactate monohydrate, said method including the steps of:
(a) combining compound 7 with hydrazine in the presence of acetic acid in methanol and THF at the temperature of about 130° C. to produce compound 8:

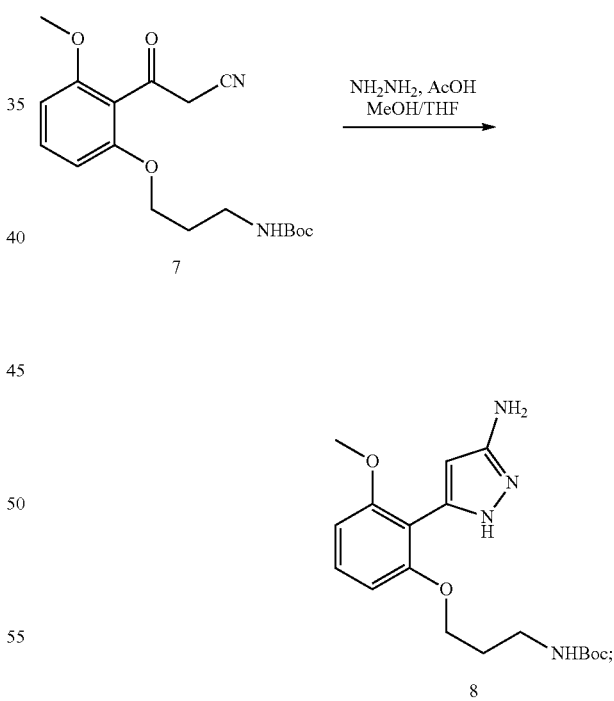

(b) combining compound 8 with compound 9 in the presence of N-ethylmorpholine in DMSO at the temperature of about 85° C. to produce compound 10:

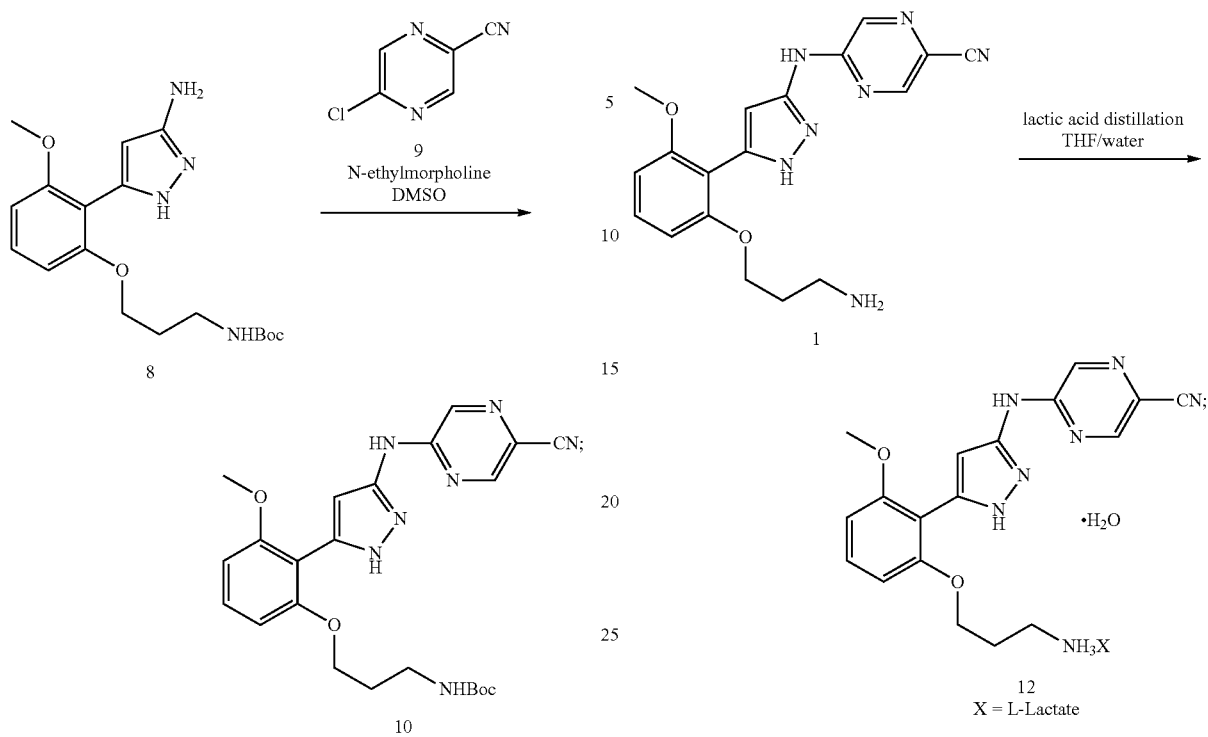

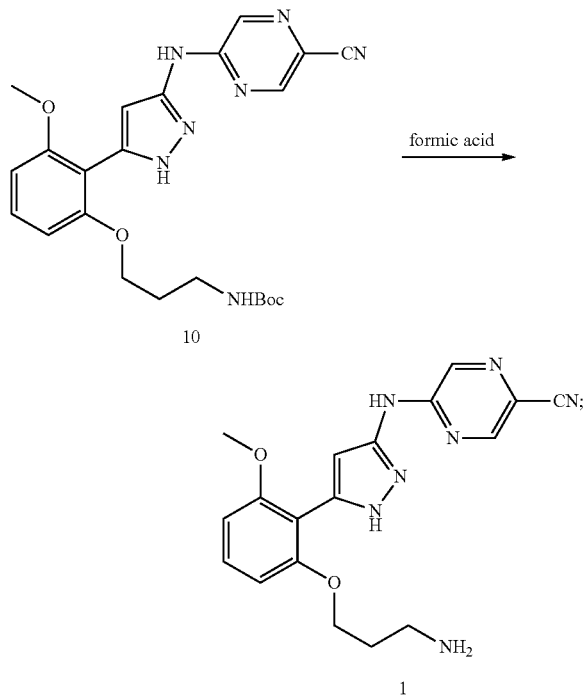

(c) deprotecting compound 10 by combining it with formic acid at the temperature of about 25° to produce compound 1:

and (d) subjecting compound 1 to lactic acid distillation in THF/water to produce compound 12:

wherein each of steps (a)-(d) is carried out in a series of units connected to each other, e.g., using tubing, to support continuous flow; and wherein said series of units includes at least one membrane-based unit.

In some embodiments, at least step (a) is carried out in a membrane-based unit. In some embodiments, at least step (b) is carried out in a membrane-based unit. In some embodiments, at least step (c) is carried out in a membrane-based unit. In some embodiments, at least step (d) is carried out in a membrane-based unit. In further embodiments, each of steps (a)-(d) is carried out in a membrane-based unit.

In some embodiments, where at least step (a) is carried out in a membrane-based unit, the membrane-based unit is a membrane-based reactor unit, e.g., a Pore Flow Through Reactor (PFTR). In some embodiments, the method further includes, after step (a), combining compound 8 with toluene and carrying out countercurrent solvent extraction using a membrane-based unit to yield compound 8 in a mixture of toluene, methanol, water and THF, wherein said membrane-based unit is a pervaporation membrane device.

In some embodiments, in a countercurrent membrane solvent extraction of compound 8 from a substantial water-containing polar solution also containing methanol and THF, toluene is passed in a countercurrent direction on the other side of the porous membrane to extract compound 8 along with some methanol and THF from the water phase (flowing in the opposite direction) which is generated by adding some water on the other side of the membrane at the other end of the extractor.

In some embodiments, pervaporation (PV) process removes volatile solvents, such as methanol, THF and toluene after addition of DMSO through a perfluoropolymer based PV membrane, prior to step (b). In some embodiments, membrane-based solvent extraction in a two-phase system results in an aqueous phase extracting the following impurities: hydrazine, acetic acid and deprotected compound 8. In some embodiments, the level of impurities achieved after extraction is hydrazine: <2 parts per million relative to the compound 8, and the deprotected compound 8 reduced to less than 1% from as much as 5% in the solution prior to extraction.

In some embodiments, the method further includes adding DMSO to compound 8 in toluene, methanol, water and THF to produce a mixture; and introducing said mixture into a membrane-based unit to remove toluene, methanol and water from said mixture by pervaporation. In some embodiments, the removal of toluene, methanol and water from said mixture by pervaporation is carried out at the temperature of about 60° C. In some embodiments, the membrane-based unit includes a perfluorocopolymer membrane.

In some embodiments, the method includes, prior to step (b), combining compound 8 with compound 9 in DMSO in a membrane-based unit to produce a mixture of compound 8 and compound 9 in DMSO, wherein the membrane-based unit is a membrane mixer. In some embodiments, the membrane mixer is a porous hollow membrane mixer. In a further embodiment, the membrane-based unit is a Pore Flow Through Reactor (PFTR). In some embodiments, when at least step (c) is carried out in a membrane-based unit, the membrane-based unit is a Pore Flow Through Reactor (PFTR). In some embodiments, when at least step (d) is carried out in a membrane-based unit, the membrane-based unit is a pervaporation membrane device. In further embodiments, the pervaporation membrane device includes a perfluorocopolymer membrane.

In some aspects, the present invention relates to a system for continuous manufacturing of prexasertib monolactate monohydrate in accordance with the method of the invention, the system includes a series of units connected to each other, e.g., using tubing, to support continuous flow, wherein at least one unit in said system is a membrane-based unit. In some embodiments, the system is 500 as illustrated in FIG. 8. In some aspects, the present invention relates to a method for continuous manufacturing of fluoxetine hydrochloride, the method includes (a) reacting compound 13 with diisobutylaluminium hydride (DIBALH) in water/hydrochloric acid at a temperature of about 25° C. to produce compound 14:

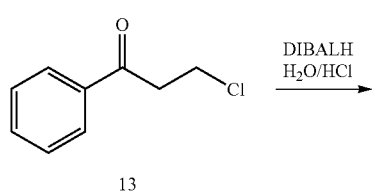

13

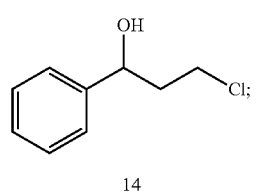

14

(b) combining compound 14 with methylamine at a temperature of about 135° C. to produce compound 15:

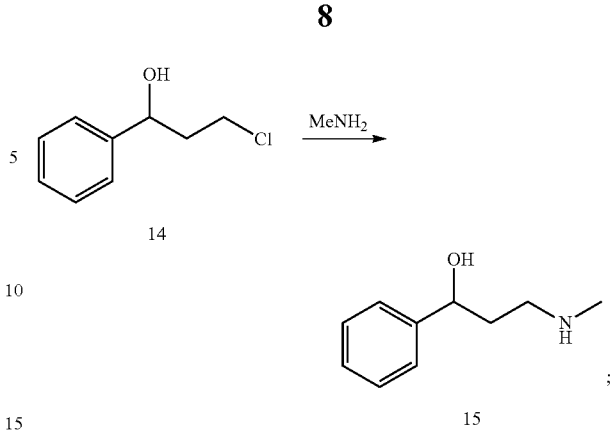

and (c) combining compound 15 with compound 16 in the presence of potassium tert-butoxide and a crown ether at a temperature of about 140° C. to produce compound 17:

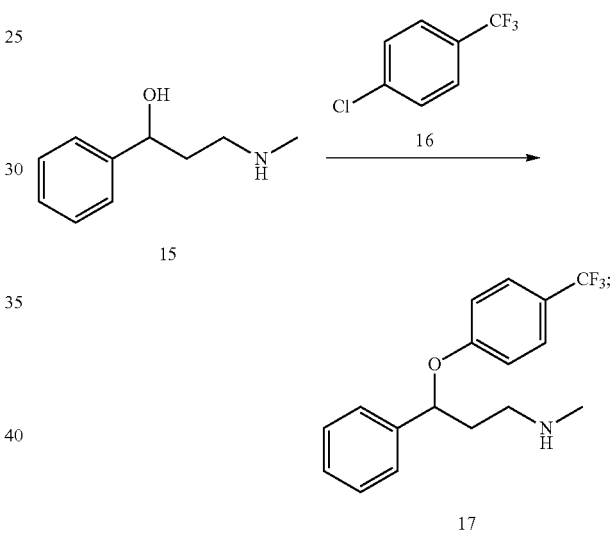

wherein each of steps (a)-(c) is carried out in a series of units connected to each other, e.g., using tubing, to support continuous flow; and wherein said series of units includes at least one membrane-based unit.

In some embodiments, at least step (a) is carried out in a membrane-based unit. In some embodiments, at least step (b) is carried out in a membrane-based unit. In some embodiments, at least step (c) is carried out in a membrane-based unit. In some embodiments, each of steps (a)-(c) is carried out in a membrane-based unit. In some embodiments, when step (a) is carried out in a membrane-based unit, the membrane-based unit is a Pore Flow through Reactor (PFTR).

In some embodiments, the method further includes performing solvent extraction-based removal of aluminum salts and other polar impurities into aqueous phase to purify compound 14 present in toluene phase by introducing a solution comprising compound 14 into a membrane-based unit, wherein said membrane-based unit is a liquid-liquid (L-L) nondispersive membrane reactor In some embodiments, the method further includes performing solvent extraction after step (b) in a membrane-based unit to produce a mixture of compound 15 in THF. In further embodiments, the membrane-based unit is a liquid-liquid nondispersive membrane solvent extraction unit (L-L MSX unit).

In some embodiments, the method further includes removing residual water left in the mixture of compound 15 in THF by passing said mixture through a membrane-based unit. In some embodiments, the membrane-based unit is a pervaporation membrane device. In some embodiments, the pervaporation membrane device includes a perfluorocopolymer membrane. In some embodiments, when step (c) is carried out in a membrane-based unit, the membrane-based unit is a Pore Flow through Reactor (PFTR).

In some embodiments, the method further includes, after step (c), extracting compound 17 with tert-butyl methyl ether (TBME) in a membrane-based unit. In some embodiments, the membrane-based unit is a liquid-liquid nondispersive membrane solvent extraction unit (L-L MSX unit). In some aspects, the present invention also relates to a system for continuous manufacturing of fluoxetine hydrochloride in accordance with methods of the invention, the system including a series of units connected to each other, e.g., using tubing, to support continuous flow, wherein at least one unit in said system is a membrane-based unit. In some embodiments, the system is 600 as illustrated in FIG. 9.

Any combination and/or permutation of these embodiments is envisioned. Other objects and features will become apparent from the following detailed description considered in conjunction with the accompanying drawings. It is to be understood, however, that the drawings are designed as an illustration only and not as a definition of the limits of the present disclosure.

BRIEF DESCRIPTION OF THE DRAWINGS

For a more complete understanding of the present invention, reference is made to the following Detailed Description of the Invention, considered in conjunction with the accompanying drawings, in which:

FIG. 6B is a schematic illustration of carrying out "Step 1" shown in FIG. 6A (Stage I). FIG. 6C is a schematic illustration of carrying out "Step 2" and "Step 3" shown in FIG. 6A (Stage II). FIG. 6D is a schematic illustration of carrying out "Step 4" shown in FIG. 6A (Stage III)

DETAILED DESCRIPTION OF THE INVENTION

As discussed herein, use of membrane-based API synthesis (as compared to traditional API synthesis) allows for considerable reduction of devices used in the process. For example, traditional solvent extraction can first involve a mixer where one phase is dispersed as drops into another phase, then dispersed in a two phase system before being taken to a settler (often gravity based) to separate the two phases. This can be problematic, besides requiring an additional device. In membrane-based solvent extraction, only one device is needed. In addition, membrane-based synthesis can be used to carry out an equilibrium-limited reaction process and change the equilibrium conversion by removing one of the products through the membrane and achieve a higher conversion and/or selectivity. (See, e.g., J. Whu et al., Modeling of Nanofiltration-assisted Organic Synthesis, J. Membrane Sci., 163(12), 319-331 (1999); see also Park, B. G. et al., Design issues of pervaporation membrane reactors for esterification, Chem. Eng. Sci., 57, 4933 (2002)). Membrane-based synthesis allows for control of the feed introduction rate, mixing of different reactants via a membrane into a membrane reactor, control of the reaction pathways, conversion, and selectivity. Membrane-based synthesis includes membrane devices that do not suffer from phase flow limitations encountered in conventional separation devices (which traditionally suffer from flooding and/or loading). Membrane-based devices can be scaled up or down easily, resulting in easier scale up or down of API manufacturing. Thus, using a membrane-based API synthesis system provides significant advantages over traditional API manufacturing.

Figure 4:
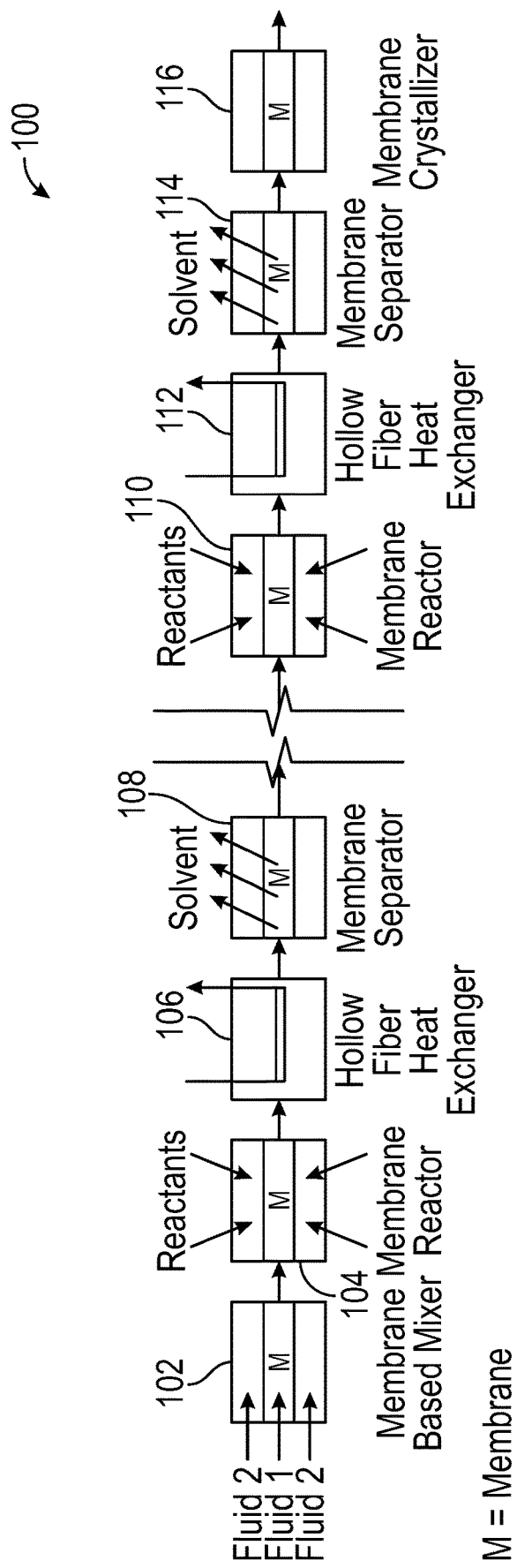
FIG. 4 is a schematic of a multistep membrane-based API synthesis in accordance with exemplary embodiments of the present disclosure.

FIG. 4 is a schematic of a multistep membrane-based API synthesis system 100 (hereinafter "system 100") in accordance with exemplary embodiments of the present disclosure. The system 100 can include a membrane-based mixer 102, a first membrane reactor 104, a first heat exchanger 106 (e.g., a hollow fiber heat exchanger), a first membrane-based solvent separator 108, a second membrane reactor 110, a second heat exchanger 112 (e.g., a hollow fiber heat exchanger), a second membrane-based solvent separator 114, and a membrane-based crystallizer 116. The system 100 therefore incorporates several membrane-based devices into the sequential steps of the process performed by the system 100. The system can incorporate all membrane-based devices to replace traditional non-membrane-based devices for the reaction processes and separation steps, which can reduce the total number of devices used overall.

Figure 3A:
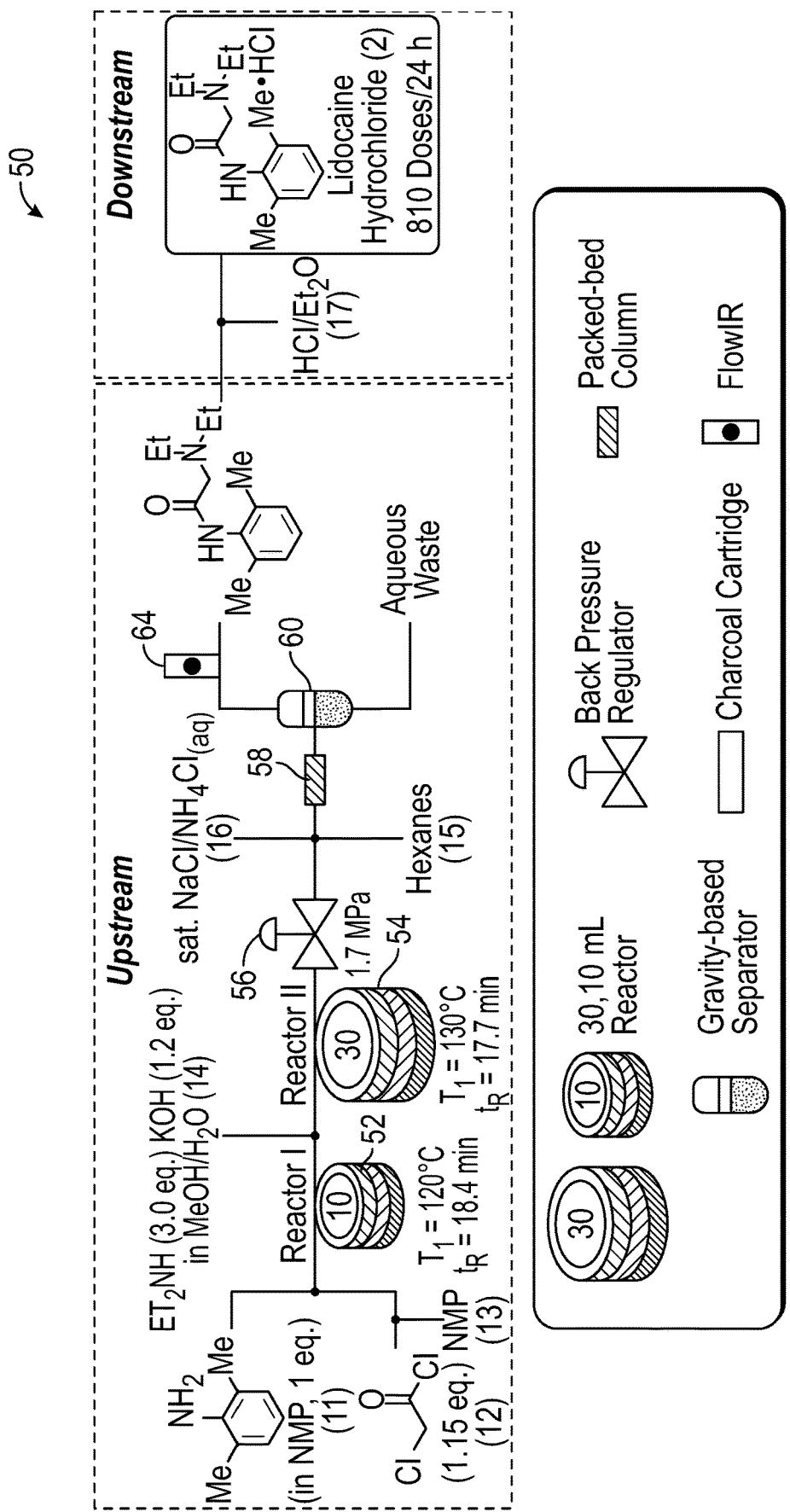
FIG. 3A is a flowchart showing the synthesis of lidocaine hydrochloride using a traditional two-step upstream system configuration.

In some embodiments, the mixer 102 can be a porous hollow fiber membrane mixer (such as the mixer FIG. 3A) instead of an inline mixer to mix neat chloroacetyl chloride (12) with N-methyl-2-pyrrolidone (NMP) and then mix it with 2, 6-xylidine (11) in N-methyl-2-pyrrolidone (NMP). In some embodiments, the membrane-based mixer 102 using porous membranes can itself be the subsequent membrane reactor 104 shown in FIG. 4, thereby acting as both the mixer 102 and reactor 104. If the synthesis reaction is significantly exothermic and requires cooling during or after the reaction, a non-porous ceramic tubule or a non-porous polymeric hollow fiber based heat exchanger 106 can be used by the system 100 to cool the post-reaction solution.

The cooled reaction product-containing solution undergoes membrane separation in the membrane separator 108, which can be of one of several types of separators. In some embodiments, if the solvent has to be exchanged with another solvent to prepare for the next synthesis reaction, the system 100 can use an organic solvent nanofiltration (OSN) with continuous addition of the replacement solvent to the flowing feed solution and removal of the solvents (as shown by the arrows extending out of the separator 108 in FIG. 4) without removing the intermediate product(s) formed in the reactor. Simultaneously, the concentration of the desired solvent increases in the feed solution to the membrane unit. In some embodiments, the system 100 can use a highly selective organic solvent reverse osmosis (OSRO) membrane in the membrane separator 108 to remove the undesired solvent through the membrane while retaining the solvent needed in the solvent exchange process. The reaction intermediate product is retained by the membrane.

Figure 3B:
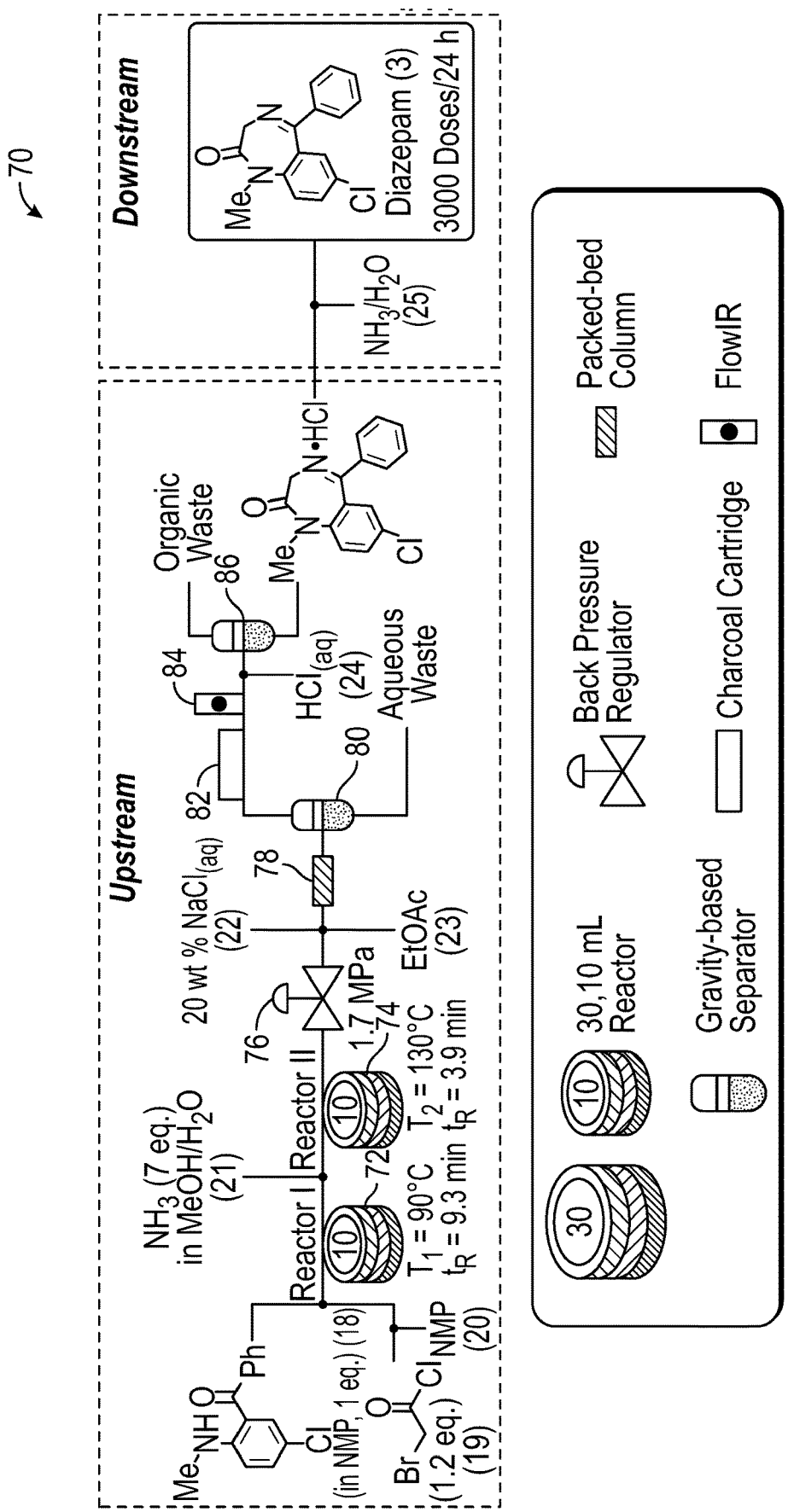
FIG. 3B is a flowchart showing the synthesis of diazepam (VALIUM®) using a traditional two-step upstream system configuration.

In some embodiments, the system 100 can use nondispersive membrane solvent extraction (MSX) in the separator 108 to remove undesirables/impurities from the reaction product stream through a porous membrane into an extracting immiscible solvent. In some embodiments, the desired intermediate product in the solution exiting the reactor 104 can be extracted into the extracting solvent through the membrane by MSX and taken to the next synthesis step of the process. Such membrane solvent extraction step combines two steps identified in FIGS. 3A and 3B as the packed-bed column and gravity-based separator into a single step/device without any dispersion of one phase into the other.

Figure 1:
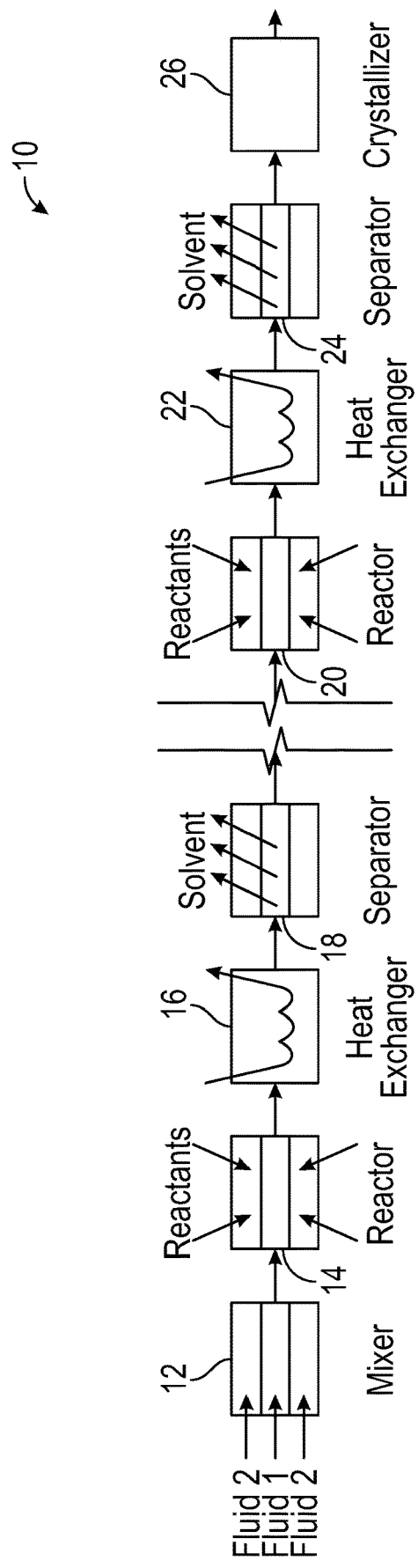
FIG. 1 is a schematic of a traditional continuous pharmaceutical production sequence of reactors and separators followed by a crystallizer.
Figure 2:
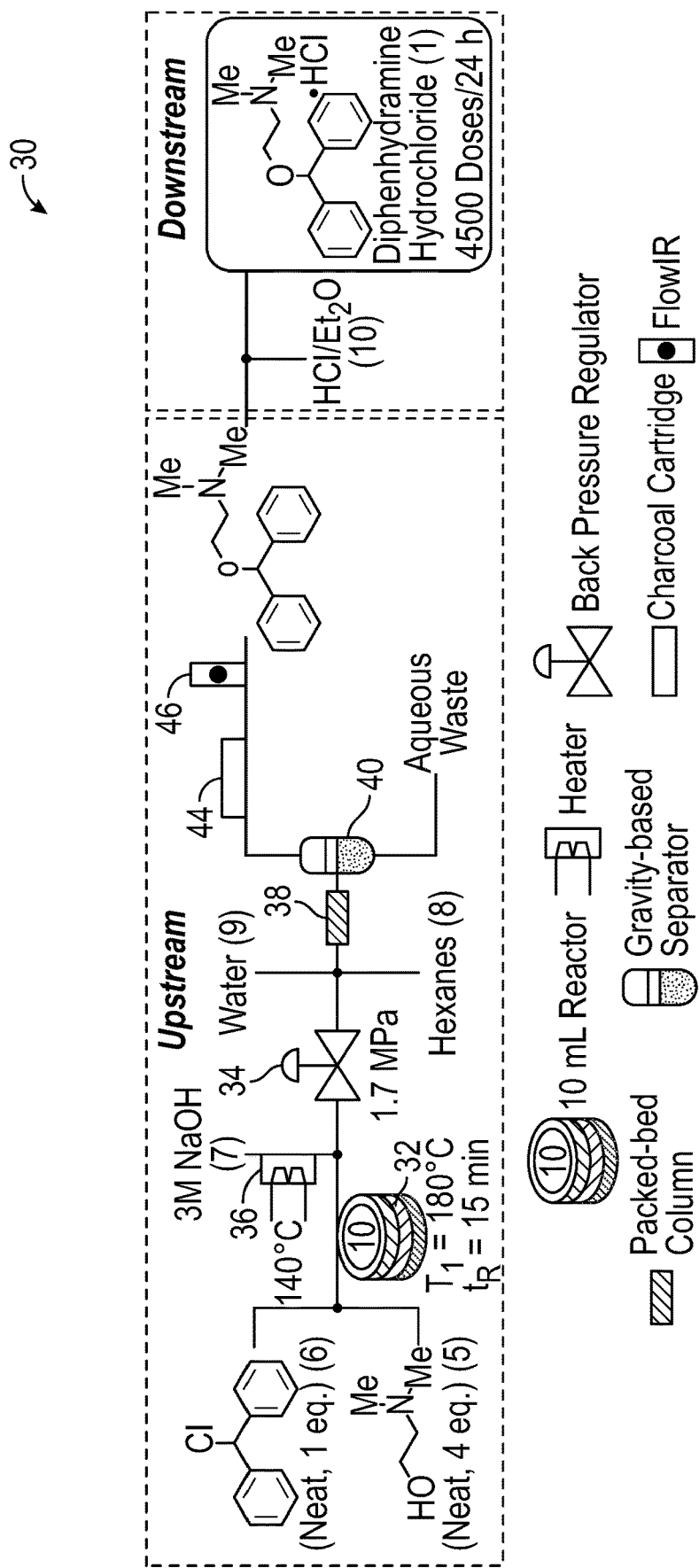
FIG. 2 is a flowchart showing the upstream and downstream synthesis of diphenhydramine hydrochloride (BENADRYL®) using a traditional reconfigurable system.

An example for such a step is provided in FIG. 2 where preheated aqueous sodium hydroxide (3M) is used to dissolve the reaction product (from the reactor), although the resulting solution contains some impurities. In particular, FIG. 2 shows the mixer 38 followed by a gravity-based settler 40. Extraction from one phase to the other phase in the mixer 38 is achieved with high interfacial area via one phase present as dispersed drops in the other phase. Using a gravity-based phase settler 40, the lighter phase goes up and the heavier phase goes down to the bottom, thus separating the two phases. Gravity-based phase separation is usually problematic, generally necessitating the use of a separate membrane separator device for phase separation. (See, e.g., M. Peer et al., Biphasic catalytic hydrogen peroxide oxidation of alcohols in flow: Scale-up and extraction, Org. Process Res. Dev., 20, 1677-1685 (2016)). This can be highly problematic in flow chemistry where in biphasic systems, one employs dispersive mode of operation which creates problems during phase coalescence. Instead of two such potentially problematic devices, membrane solvent extraction uses only one device and does not disperse one phase into the other. The phases contact each other at the membrane pore mouth without dispersion. Therefore, no gravity-based separator is needed. Extraction is far more efficient and the device size is an order of magnitude smaller without emulsion problems and consequent API precursor loss. The resulting aqueous solution is next subjected to membrane solvent extraction with hexane, extracting the desired reaction product, which later yields diphenhydramine hydrochloride after treatment with HCl.

As illustrated in FIG. 4, the membrane-based mixer 102 receives a first fluid (fluid 1) into the membrane channel, and simultaneously receives a second fluid (fluid 2) on both sides of the membrane channel. The mixer 102 includes a porous membrane (e.g., porous hollow fiber membrane) forming the walls of the membrane channel and defining the membrane channel relative to the surrounding channels for the second fluid. During the process, the second fluid is forced to pass through the pores of the membrane into the first fluid on the other side of the membrane.

Similarly, the reactor 104 includes a porous/microporous/dense membrane through which the solution passes surrounded by outer channels into which the reactants are introduced, such that the reactants are forced to pass through the pores of the membrane and into the solution. The separator 108 includes the inner sub-nanoporous membrane channel and solvent is pushed through the pores of the membrane and out of the separator 108. A similar process is repeated in the reactor 110, the heat exchanger 112, and the separator 114 (and can be repeated in additional reactors, heat exchangers, and separators) before progressing to the membrane crystallizer 116. Two or more reactants are needed for a reaction in reactor 104. These may come in through the solution. Alternatively, one or more reactants can come with the solution, and additional reactants can be slowly introduced from the outside through the pores in the membrane wall into the reactor 104. This enables achieving a controlled rate of reaction. A membrane separator can be of various types. If a solvent from the reaction media is to be removed, pressure can be applied on the solution in the membrane separator and pass the solvent and not the intermediate product through a nanofiltration membrane. Alternatively, if water has been produced in the reaction and is present as an esterification reaction, by pulling a vacuum on the other side of the membrane, water can be removed by a pervaporation process selectively through a nanoporous membrane. This increases the conversion of the process and allows one to obtain a higher yield of the intermediate product. Each of the units is the system 100 used in continuous pharmaceutical/API manufacturing therefore uses a corresponding membrane-base unit (as compared to non-membrane units in traditional continuous API manufacturing systems). Essentially every step in the continuous pharmaceutical/API synthesis processes discussed herein can be implemented continuously and efficiently using membrane technologies and membrane-based processes.

Membranes used by the system can be of various types depending on the needs of the user and/or end product. A nonporous membrane can be used, but allows small molecules and/or solvents to go through (as in reverse osmosis process and pervaporation process) when pressure is applied to the feed solution and/or vacuum is pulled on the other side. The transport corridors in the nonporous membrane can be slightly increased in nanofiltration membranes to allow larger molecules of molecular weight of up to about 1,100 Dalton to not go through the membrane, while solvents pass through much faster. Membranes having larger transport corridors appropriately termed pores can be used for a variety of separations, such as ultrafiltration. Membranes having these types of somewhat larger pores can be used for mixing, membrane solvent extraction, or the like.

In some embodiments, only one device used in the continuous pharmaceutical/API manufacturing system 100 is replaced by a corresponding membrane-based unit. In instances where only one or two devices in the system 100 are replaced by membrane-based units (e.g., not all possible units are membrane-based), the API manufacturing process continues to be improved as compared to traditional synthesis, but may result in less conversion, less recovery, and potentially more operating problems (as compared to a fully membrane-based process). For example, the packed bed and the gravity separator used in conventional continuous pharmaceutical/API manufacturing (e.g., FIGS. 2, 3A, and 3B) can be replaced by a membrane solvent extraction device. As another example, consider a porous/microporous membrane. If it is hydrophobic, its pores are more likely to be wetted by the organic phase being used in the solvent extraction and flowing on one side of the membrane. If an aqueous phase flows on the other side of the membrane at a pressure equal to or higher than that of the organic phase, then the membrane-wetting organic phase cannot appear on the other side of the membrane where the aqueous phase is flowing. However, the phase interface between the organic and aqueous phase is immobilized at the membrane pore mouth. Then, solvent extraction or back extraction can take place across this aqueous-organic phase interface from the aqueous to the organic, or the organic to the aqueous phase, respectively. As long as the aqueous phase pressure does not exceed that of the organic phase by an amount exceeding a breakthrough pressure, the aqueous-organic phase interface remains immobilized and nondispersive solvent extraction takes place. There is no need for a settler as in gravity-based separator/settler used in FIGS. 2, 3A and 3B.

Alternatively, various other dispersive solvent extraction devices of the system 100 (such as a mixer and/or a settler) can be replaced by a membrane solvent extraction (MSX) device. In some embodiments, only certain devices used in continuous pharmaceutical/API manufacturing can be replaced by corresponding membrane-based units. In some embodiments, one group of components (e.g., mixer, reactor, heat exchanger and separator) can be membrane-based, while a subsequent group of components can be non-membrane-based. However, at least two steps of the exemplary process and system incorporate a membrane-based device and process.

In some membrane-based devices, referred to as membrane contactors, the membrane contactor device facilitates the conventional reaction/separation step by bringing two immiscible phases into contact without any dispersion of one phase into the other phase. Because dispersion is eliminated, coalescence of the phases is no longer required.

While phase contacting generally requires dispersion of one immiscible phase into another immiscible phase, a porous membrane contactor can eliminate dispersion and yet provides a contacting surface area between the two phases that can be up to 5-20 times what is achieved in a dispersion-based device. Membrane contactor-based devices can also prevent emulsion formation when contacting two immiscible liquid phases. However, if contacting requires creating an emulsion, porous membrane-based devices can achieve such emulsion with a much higher control over the size of the emulsion droplets. In addition, the membrane contactors can bring two miscible phases into intimate contact and achieve mixing, thereby developing a membrane mixer (such as mixer 102 of FIG. 4).

Catalytic or noncatalytic gas-liquid reactions, such as hydrogenation, aerobic oxidation, carboxylation using $CO_2$, and ozonation, can be carried out in a tubular and hollow fiber membrane contactor, and can easily accommodate scale-up. Catalytic or noncatalytic liquid-liquid reactions requiring mixing of two miscible liquid phases can be carried out with excellent mixing efficiency in a porous hollow fiber membrane-based device mixer, such as a membrane mixer 102, or a flat membrane-based device. One of the streams to be mixed can be introduced in a distributed fashion through the membrane pores into the other stream flowing on the other side of the membrane. This allows for an increased level of control.

It will be understood that such membrane-based reaction devices can be short or long to accommodate the needs of the reaction, residence time requirement, combinations thereof, or the like. It will also be understood that several membrane-based reaction devices can be combined in different methods/systems to accommodate the needs of the reaction. For example, short reactors can be followed by solid polymeric hollow fiber membrane-based heat exchangers, dense ceramic tubule-based heat exchangers, or conventional heat exchangers for exothermic reactions. Therefore, in some embodiments, a short reactor can be used followed by a heat exchanger, followed by another short reactor, followed by another heat exchanger, and so on until the desired conversion is attained.

After each synthesis step in a conventional pharmaceutical synthesis, the solvent may need to be exchanged and the catalysts may need to be replaced before the next reaction step. Such work-up involves a significant number of separation steps, including distillation, solvent extraction, and adsorption, which complicates the synthesis process and can have a negative effect on the resulting API. Using the system 100, such separation steps can be implemented at near room temperature using porous membrane-based nondispersive membrane solvent extraction (MSX) or dense or relatively dense polymeric membranes through nanofiltration (OSN), reverse osmosis (OSRO), pervaporation, combinations thereof, or the like. If a volatile solvent (including water) must be removed, membrane pervaporation can be implemented to selectively remove the volatile solvent from the feed mixture through the membrane. If the solvent must be removed and the intermediate compound must be concentrated, organic solvent nanofiltration (OSN) can be used. If solvent exchange must be implemented, OSN can be used in the diafiltration mode with the exchange solvent introduced. Alternately, after the exchange solvent is introduced, the system 100 can use organic solvent reverse osmosis (OSRO) to remove the undesired solvent through a solvent-resistant reverse osmosis membrane at room temperature.

Conventional membrane operations are intrinsically continuous. Membrane devices are scalable, and can be scaled up or down. The membrane devices can carry out the reaction-separation and associated steps in API synthesis in a continuous manner. The steps of an exemplary embodiment of the continuous production of APIs can include (1) membrane solvent extraction; (2) reverse osmosis (RO) and nanofiltration (NF); (3) membrane pervaporation; (4) membrane mixing; (5) membrane reactors; (6) enzymatic synthesis; (7) hollow fiber heat exchangers; (8) membrane adsorption; and (9) membrane crystallization. Membrane fouling is considered after describing these membrane-based steps. Each of the steps is described in greater detail herein.

In some embodiments, a membrane solvent extraction (MSX) device can be used. MSX devices can replace a packed-bed column-based solvent extractor and a gravity settler, which are used in the processes shown in FIGS. 2 and 3A-3B. Hollow fiber (HF) microporous membrane-based devices can be used for non-dispersive solvent extraction (NDSX), which removes the need for a gravity-based separator. (See, e.g., Sirkar, K. K. Membranes, phase interfaces and separations: Novel techniques and membranes—An overview, I&EC Res., 47, 5250-5266 (2008)). MSX devices are significantly smaller than dispersion-based devices, and they do not suffer flooding or loading issues. Additionally, MSX devices can have almost any flow rate ratio between the two immiscible phases flowing on two sides of the membrane. Wider commercialization of such devices has not been achieved due to non-availability of membranes that are resistant to many pharmaceutically relevant solvents. At present, polytetrafluoroethylene (PTFE)-based microporous membranes having smaller pore sizes are in the marketplace and can be used by the system 100. (See, e.g., Singh, D. et al., High temperature direct contact membrane distillation-based desalination using PTFE hollow fibers, Chem. Eng. Sci., 116, 824-833 (2014)). Reduction of the membrane pore size via novel strategies would allow extraordinary flexibility in NDSX operation and application.

Following synthesis, solvent exchange is generally needed. Solvent exchange is generally carried out by distillation, either vacuum-based or otherwise. In some embodiments, the exchange can be conducted athermally because pharmaceutical intermediates and APIs are thermally sensitive. In some embodiments, the next solvent can be added to the mix and then the previous solvent is taken out through an appropriate membrane by organic solvent reverse osmosis (OSRO) at about 25° C. Recent results have shown that with a particular perfluoropolymer membrane, pure toluene can be obtained as permeate from its binary mixtures with polar aprotic solvents, such as NMP, DMSO, and DMF, at pressures around 3,500-4,000 kPa. (See, e.g., Chau, J. et al., Reverse osmosis separation of particular organic solvent mixtures by a perfluorodioxole copolymer membrane, J. Membrane Sci., 563, 541-551 (2018)). Pressures used in commercialized RO desalination are often much higher. Research has shown that pure methanol is obtained as permeate from its binary mixtures with polar aprotics, e.g., NMP. See id. Further, recent MD simulations of organic solvent nanofiltration (OSN) membranes have proven to be inadequate, as these membranes have no selectivity for organic solvent mixtures (OSMs). (See, e.g., Liu, J. et al., A molecular simulation protocol for swelling and organic solvent nanofiltration of polymer membranes, J. Membrane Sci., 573, 639-646 (2019)).

Concentration of the APIs in the solvent can be achieved by using organic solvent nanofiltration (OSN) membranes enabling athermal removal of one or more solvents or an exchange with another solvent for APIs during API synthesis. (See, e.g., Marchetti P. et al., Molecular separation with organic solvent nanofiltration: A critical review, Chem. Rev. 114, 10735-10806 (2014); Sheth, J. et al., Nanofiltration-based diafiltration process for solvent exchange in pharmaceutical manufacturing, J. Membrane Sci., 211(2), 251-261 (2003)). Membranes for such steps are demanding for polar aprotic solvents and therefore require significant research. Production of numerous OSMs is ubiquitous in API synthesis. Thus, advanced membranes for pressure-driven OSN and OSRO processes can allow athermal operation and simultaneously achieve significant energy efficiency. OSN membranes that reject Jacobsen catalyst (622 Da), Wilkinson catalyst (925 Da), and Pd-BINAP (849 Da) can be used to remove the intermediate product and the solvent while holding back the larger size catalyst. (See, e.g., Scarpello, J. T. et al., The separation of homogeneous organometallic catalysts using solvent resistant nanofiltration, J. Membrane Sci. 203:71-85 (2002); Wong, H. T. et al., Recovery and reuse of ionic liquids and palladium catalyst for Suzuki reactions using organic solvent nanofiltration. Green Chem., 8, 373-399 (2006); Luthra, S. S. et al., Homogeneous phase transfer catalyst recovery and re-use using solvent resistant membranes. J. Membrane Sci., 201:65-75 (2002)).

Membrane pervaporation can be used by the system 100 during synthesis to remove unneeded solvents, such as water and volatile solvents, from the solution containing the API or other pharmaceutical intermediate. The pervaporation device can be incorporated into one or both of the membrane-based separator 108, 114 of FIG. 4. The pervaporation membrane allows volatile solvent to be removed through the membrane from the medium obtained after the reaction is completed. A typical volatile solvent removed is water. The pervaporation membrane can also be incorporated into and implemented in the reactor itself. The membrane pervaporation device can include dense membranes and a vacuum. In one embodiment, membrane pervaporation can be conducted at about room temperature. Continuous production of anhydrous tert-butyl hydroperoxide in nonane is one example of this process. (See, e.g., Li, B. et al., Continuous production of anhydrous tert-butyl hydroperoxide in nonane using membrane pervaporation and its application in flow oxidation of a γ-butyrolactam, Org. Process Res. Dev., 22, 707-720 (2018)).

To transition from batch processing in stirred tank reactors to continuous reactions, static mixer-aided tubular metallic reactors as well as microreactors are being studied extensively. (See, e.g., LaPorte, T. L. et al., Process development and case studies of continuous reactor systems for production of API and pharmaceutical intermediates, Chap. 23, pages 437-455, in Am Ende, D. (Ed.), "Chemical Engineering in the Pharmaceutical Industry: R&D to Manufacturing", John Wiley & Sons, Hoboken, NJ (2011)). Mixing various reactants is an integral step before such liquid-liquid reactions. In some embodiments, thermally and chemically inert porous hollow fiber membranes (HFMs) and ceramic tubular membranes can be used by the system 100 to achieve extraordinary mixing of two liquid phase reactant streams flowing on two sides of the membrane and can carry out synthesis under controlled conditions. The use of a porous HFM to achieve high mixing efficiency of two liquid streams on one side of the membrane has been shown with miscible aqueous and selected organic phases under room temperature conditions. (See, e.g., Chen, D. et al., Hydrodynamic modeling of porous hollow fiber anti-solvent crystallizer for continuous production of drug crystals, J. Membrane Sci., 556, 185-195 (2018a); Fern, J. C. W. et al., Continuous synthesis of nano-drug particles by antisolvent crystallization using a porous hollow-fiber membrane module, Int. J. Pharmaceut, 543, 139-150 (2018); Zarkadas, D. M. et al., Antisolvent crystallization in porous hollow fiber devices, Chem. Eng. Sci., 61(15), 5030-5048 (2006)).

Membrane emulsification can be used to mix immiscible phases requiring an emulsion-containing feed phase in a membrane reactor. (See, e.g., Joscelyne, S. M. et al., Membrane emulsification: a literature review. J. Membrane Sci. 2000, 169, 107-117). The immiscible phase is forced through the membrane pores into the reaction media on the other side of the membrane. Such membrane emulsification can be incorporated into the mixer 102.

The membrane reactor 104 can be used to/for, e.g., separate products from the reaction mixture, separate a reactant from a mixed stream for introduction into the reactor, control addition of one reactant or two reactants to the stream, nondispersive phase contacting with reaction at the phase interface or in the bulk phases, segregation of a catalyst and cofactor in a reactor, immobilization of a catalyst in or on a membrane, combinations thereof or the like. In some embodiments, the membrane can be the catalyst and/or the reactor. In some embodiments, the mixing device (e.g., mixer 102) can be the reactor 104 itself.

For miscible liquid phase-based reactions and gas-liquid reactions, such as hydrogenation, in pharmaceutical synthesis, porous tubular ceramic and porous HFM-based devices can simultaneously immobilize catalysts, achieve high mixing efficiency and controlled synthesis. Membrane-based ozonation has previously been used for water treatment. (See, e.g., Shanbhag, P. V. et al., Membrane-based ozonation of organic compounds, I&EC Res., 37(11), 4388-4398 (1998)). Membrane reactors are useful for pharmaceutical synthesis using simple hollow fiber, membrane modules of inert polymers, e.g., PTFE and ceramic membranes having hydrophobized surfaces.

Enzymatic catalysis can be used by the system 100 during enantioselective synthesis in API production. A multiphase/extractive hollow fiber membrane bioreactor has been used for enzymatic resolution of a diltiazem precursor, a poorly aqueous soluble ester, which was hydrolyzed to an alcohol via an immobilized lipase and extracted by MSX into an aqueous stream. (See, e.g., Lopez, J. L. et al., A multi-phase/extractive enzyme membrane reactor for production of diltiazem chiral intermediate, J. Membrane Sci. 1997, 125, 189-211). In a recent study involving synthesis of β-lactams that had undergone site-selective C—H amidation using cytochrome P450 enzymes obtained by directed evolution, it would have been useful to employ a membrane reactor (similar to the reactor of the exemplary system 100) retaining the enzyme. (See, e.g., Cho, I. et al., Site-selective enzymatic C—H amidation for synthesis of diverse lactams, Science, 364 (6440), 575-578 (2019)). In a membrane reactor lined with charged nanofiltration (NF) membranes for aqueous solutions, smaller molecule substrates and products flow through the NF membrane, while the enzyme and coenzyme are contained within the enzyme reactor. (See, e.g., Nidetzky, B. et al., Continuous enzymatic production of xylitol with simultaneous coenzyme regeneration in a charged membrane reactor. Biotechnol. Bioeng. 1996, 52, 387-396). Site-directed mutagenesis and membrane pores and surfaces can be used to enhance enzyme life by immobilization.

Hollow fiber heat exchangers used by the system 100 allow for heating, cooling, and/or quenching of API-containing solutions. In some embodiments, the hollow fiber heat exchanger can be made of inert dense ceramic/polymeric material. However, other suitable materials can be used for the heat exchanger. Polymeric hollow fiber heat exchangers (PHFHEs) demonstrated conductance/volume ratios 3-10 times higher than shell-and-tube devices accompanied by low-pressure drops, reaching as low as 1 kPa/NTU for lower temperature applications. (See, e.g., Zarkadas, D. et al., Polymeric hollow fiber heat exchangers (PHFHEs): An alternative for lower temperature applications, I & EC Res., 43, 8093-8106 (2004a); Song, L. et al., Polymeric hollow fiber heat exchangers for thermal desalination processes, I&EC Res., 49, 11961-11977 (2010)). Thermally stable solvent-impermeable solid hollow fiber membranes, such as PTFE, can provide efficient heat-exchange where fouling-based thermal resistance is of limited effect. Dense ceramic membrane tubules can achieve heat exchange over much higher temperatures.

Membrane-based adsorbers can be used by the system 100 to exploit convective flow through membrane pores. The membrane-based adsorbers can be incorporated into one or both of the separators 108, 114 of FIG. 4. For example, the adsorbers can be used to remove trace levels of homogeneous catalysts and allow for their recovery and reuse. Membrane-based adsorbers can be used to remove impurities from organic process streams during pharmaceutical synthesis. Membrane-based adsorption processes have been adopted to produce biopharmaceuticals, either for adsorptive purification of monoclonal antibodies (mAbs) or adsorptive removal of impurities from the mAb-containing solution/suspension. The technique is advantageous in its maximum utilization of the available sorption capacity and the rapidity with which it takes place. However, such traditional techniques have not been used with a continuous process and need additional columns for continuous operation.

Membrane crystallization performed by the crystallizer 116 of the system 100 is an essential step in API production as the production of dosage form kicks in. Membrane crystallization straddles two branches of pharmaceutical manufacturing. Crystallization can be implemented continuously using HFMs at around room temperature and pressure conditions using anti-solvent crystallization or cooling crystallization. Porous HFMs can be used to continuously crystallize APIs using anti-solvent crystallization, which allows for continuous nanocrystal production (if needed). Polymeric solid HFMs impermeable to the solvents can be used to achieve continuous cooling crystallization as PHFHE. Scale-up to increase the production rate in such membrane devices can be implemented with either an increase in the number of hollow fibers in a larger shell or having a few units in parallel, since membrane devices are modular.

Membrane fouling can occur during API production as the fluid phase can be complex with substances including dispersed particles, precipitates, and emulsions. Membrane fouling and its mitigation in pressure-driven membrane systems is consistently discussed in the industry. Membrane fouling of this type is much less present in membrane contactor-based operations. Reducing membrane fouling in the system 100 allows for enhanced success of membrane-based approaches for multi-step API synthesis. Recent cross-flow hollow fiber membrane-based desalination studies on concentrating seawater to the level of 18-19% salt was achieved without any flux reduction despite the scaling salt precipitates of $CaCO_3$ and $CaSO_4$ floating around. (See, e.g., Song, L. et al., Pilot plant studies of novel membranes and devices for direct contact membrane distillation-based desalination, J. Membrane Sci., 323, 257-270 (2008); Li, L. et al., Desalination performances of large hollow fiber-based DCMD devices, I&EC Res., 56, 1594-1603 (2017); Singh, D. et al., Novel cylindrical cross-flow hollow fiber membrane module for direct contact membrane distillation-based desalination, J. Membrane Sci., 545, 312-322 (2018)).

In some embodiments, reactor configurations using a membrane device can be used. For example, the system 100 can include a 91 m long plug-flow reactor using a 4.57-mm-ID stainless steel tubing to condense a nitrile compound with an excess of hydrazine at 130° C., 500 psig; with the residence time in the reactor of 1 hr. (See, e.g., Cole, K. P. et al., Kilogram-scale prexasertib monolactate monohydrate synthesis under continuous-flow CGMP conditions, Science, 356, 6281, 1144-1150 (2017)). Such single-phase reaction can be carried out in a membrane pore operating as if a plug flow reactor is provided with each pore.

Figure 5:
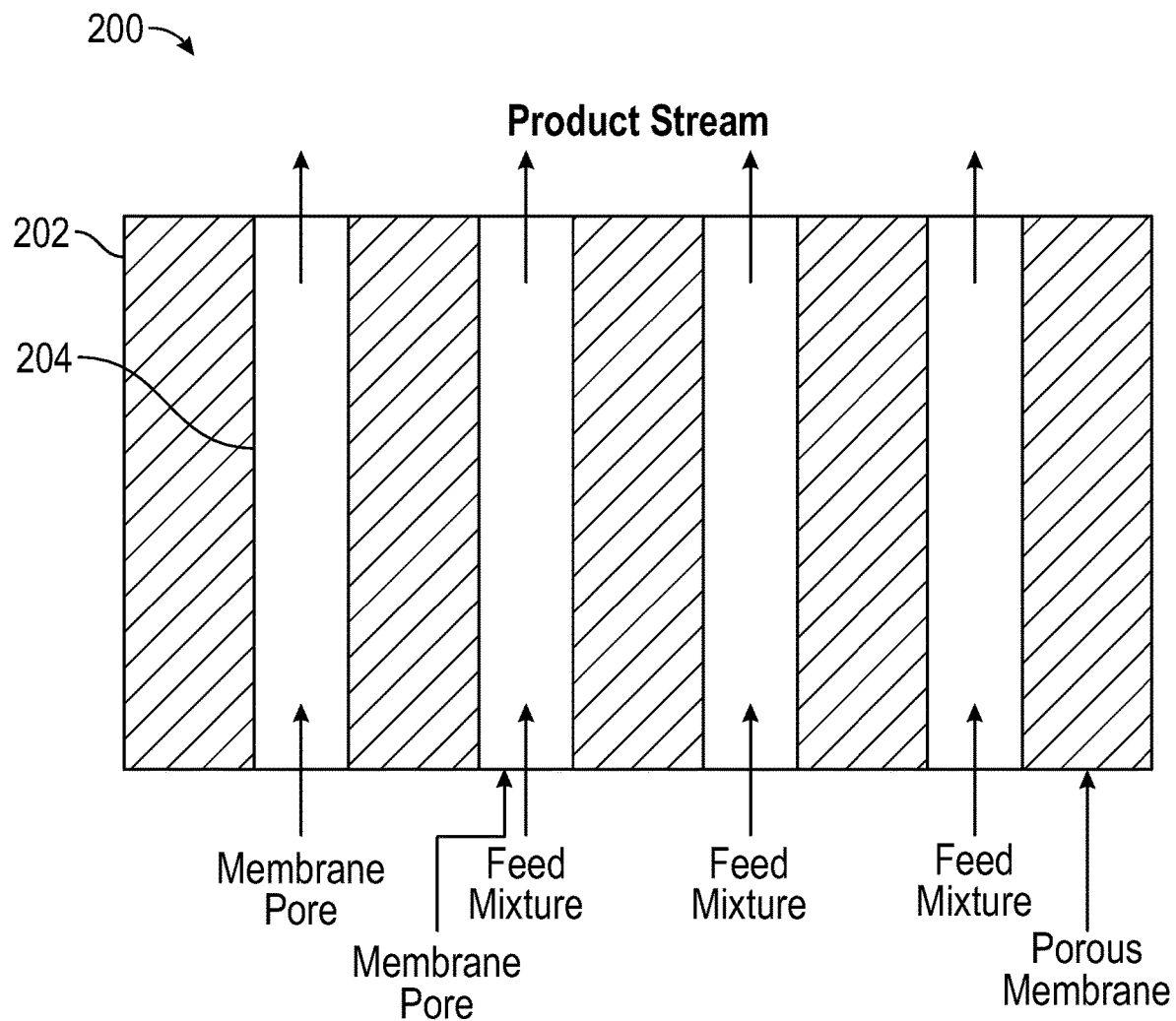
FIG. 5 is a schematic of a dead end flow configuration of a porous ceramic membrane disk-based reactor operating as a plug flow reactor capable of being incorporated into the exemplary API synthesis system.

In some embodiments, a porous alumina membrane disk can be used for a reactor of the system 100. However, it will be understood that other reactors can be used. FIG. 5 shows a schematic of a dead end flow configuration of a porous ceramic membrane disk-based reactor 200 operating as a plug flow reactor. The reactor 200 can be incorporated into the system 100 as one of the reactors used in the API manufacturing process. The reactor 200 can include a disk body 202 with multiple pores 204 extending through the body 202. The body 202 can itself form a porous membrane capable of permitting passage of liquid through the pores of the body 202. The pores 204 extend from one side to the opposing side of the body 202 to allow passage of the feed mixture therethrough. The reactor 200 is referred to herein as a pore flow through reactor (PFTR). In the porous alumina ($Al_2O_3$) membrane disk of FIG. 5, each pore 204 acts as a separate plug flow reactor. The system 100 can be used to deposit metallic or oxide catalysts on the pore 204 wall surface for catalytic reactions. The pore L/D ratio in the ceramic disk can be as high as $10^3$-$10^4$ or even higher to provide the L/D ratio used in the stainless steel/PFA tubing. (See, e.g., Cole, K. P. et al., Kilogram-scale prexasertib monolactate monohydrate synthesis under continuous-flow CGMP conditions, Science, 356, 6281, 1144-1150 (2017)). Such a reactor can have an additional advantage in case the feed has suspended material having dimensions larger than the pore 204 dimensions (discussed in the following paragraph below)

In some embodiments, to accommodate larger flow rates or longer reactor lengths, a ceramic monolith can be used for the reactor. In some embodiments, the reactor of the system 100 can be in the form of a stack of porous ceramic disks of small length and larger cross-sectional area, allowing the disks to function as a plug flow reactor. In some embodiments, the bulk feed mixture can flow tangentially over the ceramic membrane disk in a recirculation mode as if the membrane were a cross-flow filter for a system containing particulate material, which would be rejected by the small size membrane pores. The reactor can be jacketed in an appropriate environment to maintain the thermal conditions needed in an appropriate pressure environment.

After each reaction, membrane separation steps can be coupled with the membrane reactor output and separations/purifications of the intermediates/API can be carried out by the system 100. Having the membrane reactors at each synthesis step can significantly enhance reactions in a multistep API synthesis and production process, with the reactors further supported by membrane separations at each post-reaction processing step. When a membrane reactor improves the selectivity or increases the conversion, the amount of API manufactured is increased. Correspondingly, the load on the separation step(s) downstream of every membrane reactor is decreased as the purification demands are reduced. Thus, use of membrane-based reactors at the synthesis steps provides significant advantages to the final API manufactured in terms of quantity and quality. All of these steps can be carried out continuously to continuously manufacture APIs.

Example of a Membrane-Based Manufacturing of APIs

A dead-end flow configuration of a porous ceramic membrane disk-based reactor operating as a plug flow reactor is shown in FIG. 5. This membrane can replace the 91 m long plug-flow reactor (as previously used in Cole, K. P. et al., Kilogram-scale prexasertib monolactate monohydrate synthesis under continuous-flow CGMP conditions, Science, 356, 6281, 1144-1150 (2017)) by using a 4.57-mm-ID stainless steel tubing for condensation of a nitrile compound 7 with an excess of hydrazine at 130° C., 500 psig to produce the compound 8 needed during the synthesis of prexasertib monolactate monohydrate. This is shown in greater detail in FIG. 6B and discussed below.

Figure 6A:
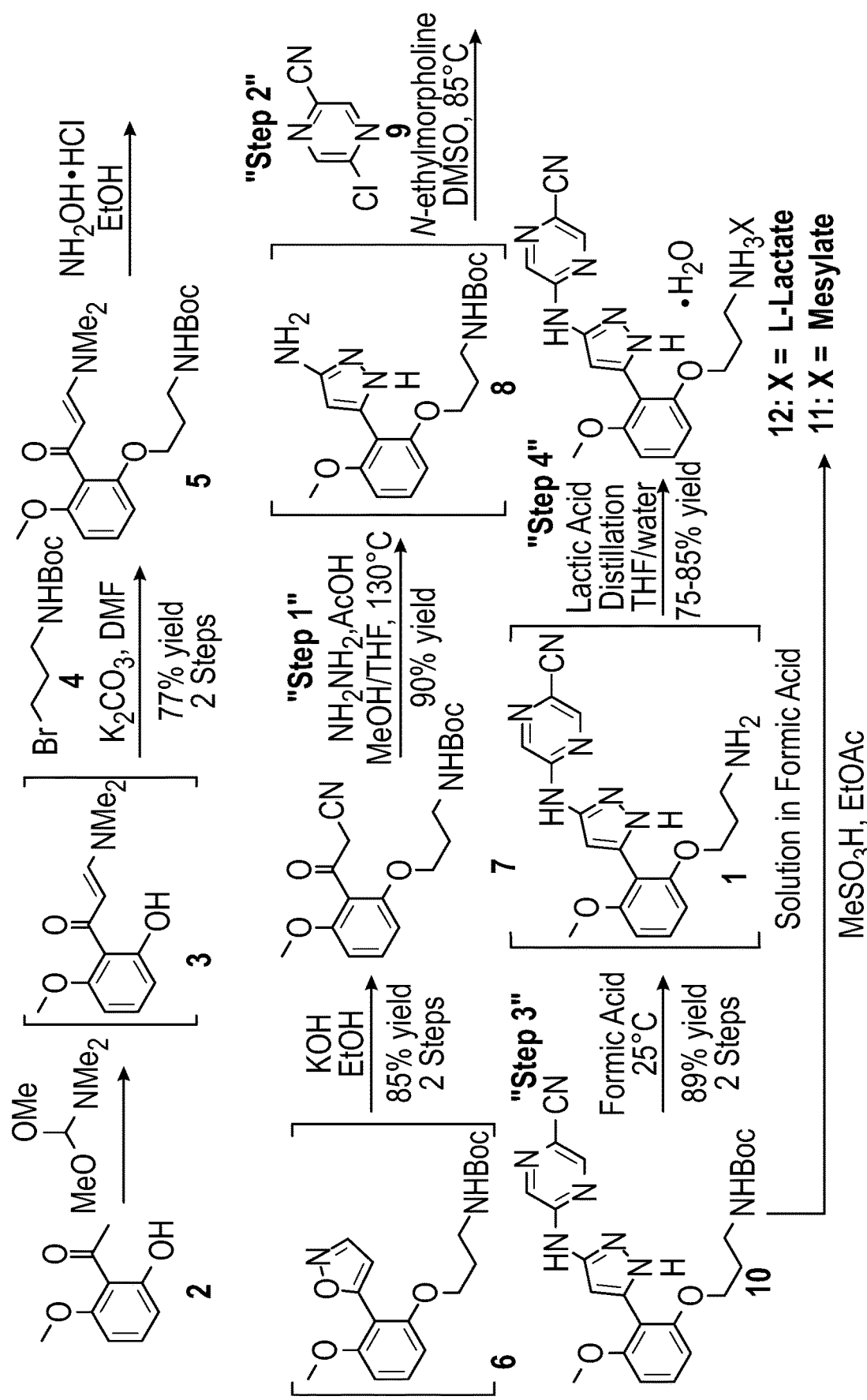
FIG. 6A is a schematic illustrating the synthetic route for a continuous manufacturing production of prexasertib monolactate monohydrate as described in Cole et al., *Science* 356, 1144-1150 (2017), the entire contents of which are hereby incorporated herein by reference.
Figure 6B:
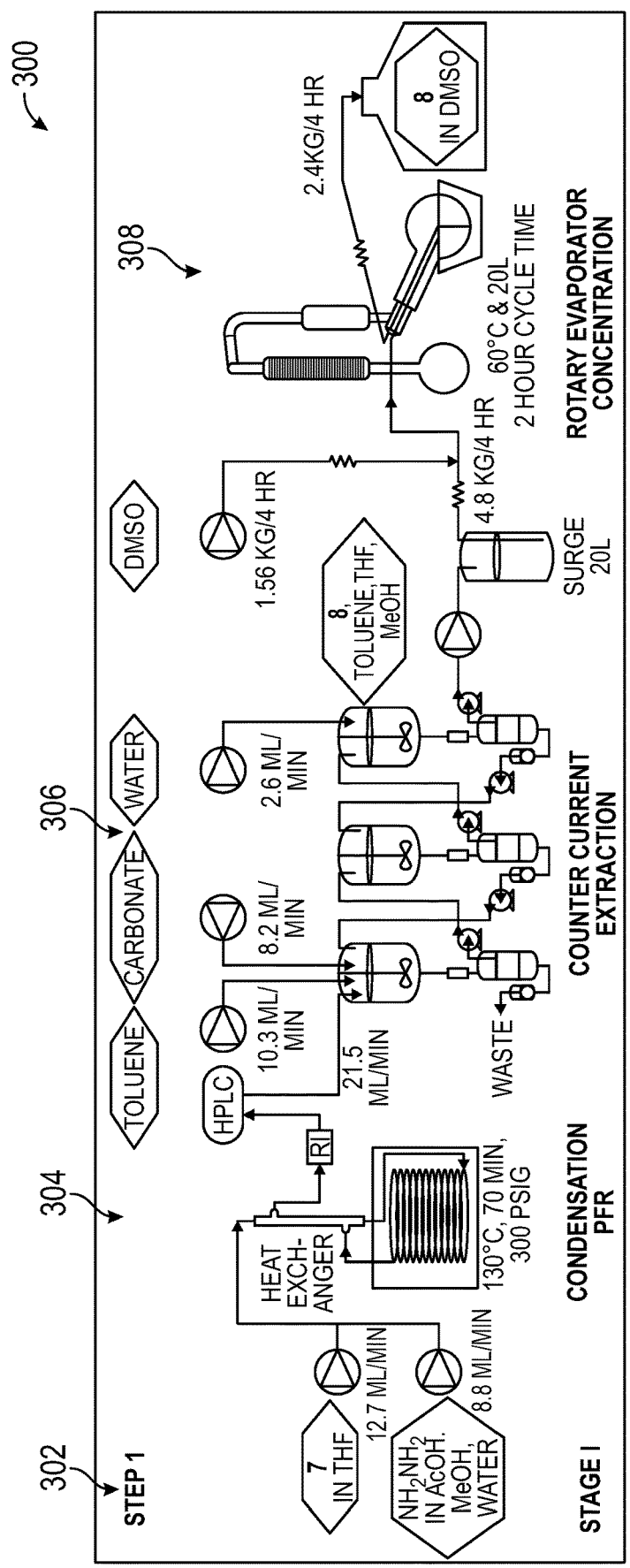
FIGS. 6B-6D are schematic illustrations of continuous manufacturing of prexasertib monolactate monohydrate in accordance with the synthetic route shown in FIG. 6A. Specifically.
Figure 8:
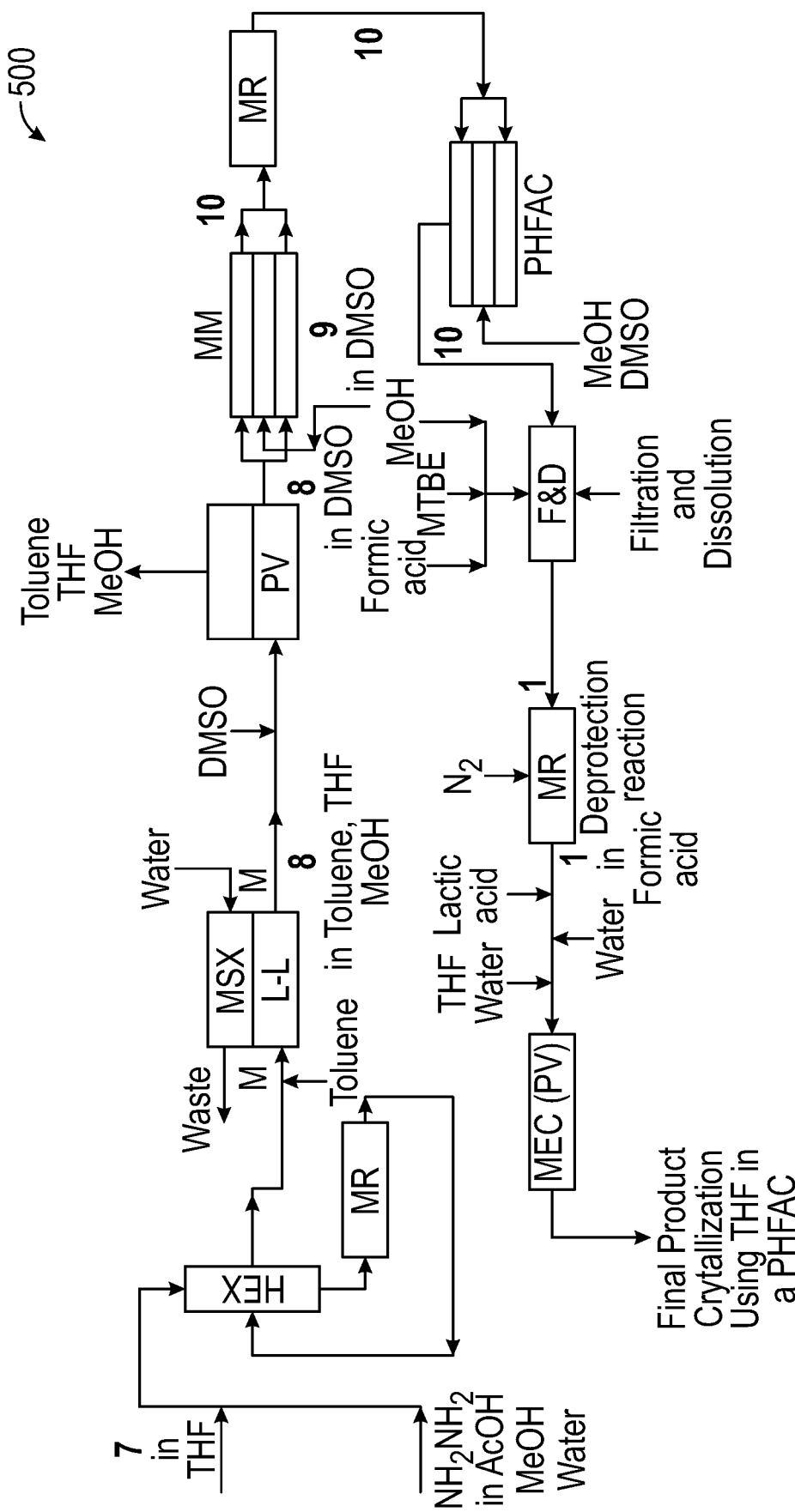
FIG. 8 is a schematic of membrane-facilitated continuous manufacturing operation for Prexasertib Monolactate Monohydrate.

FIG. 6B is a schematic illustrating the synthetic route for continuous manufacturing of Stage I synthesis process 300 capable of being performed by the exemplary system. (See, e.g., Cole, K. P. et al., Kilogram-scale prexasertib monolactate monohydrate synthesis under continuous-flow CGMP conditions, Science, 356, 6281, 1144-1150 (2017)). In comparison, the exemplary system provided in FIG. 8 illustrates the simpler and smaller implementation of membrane-based synthesis. Still with reference to FIG. 6B, Stage I begins as input 302 at step 1 to the condensation PFR section 304, which progresses to the counter current extraction section 306, and finally enters the rotary evaporator concentration section 308. The product is initially cooled down in a dense ceramic tubular membrane heat exchanger or PTFE hollow fiber heat exchanger as it heats up the feed going into the PFR discussed previously. After cooling the product in a PTFE hollow fiber heat exchanger or a dense ceramic tubular membrane heat exchanger, toluene is added to the organic stream containing compound 8 for countercurrent solvent extraction while water is added from the other end of the mixer settler countercurrent extraction cascade (shown in FIG. 6B). A single porous hollow fiber membrane solvent extraction device can be used in the system of FIG. 8 to carry out continuous countercurrent extraction efficiently (instead of using a 6-device 3-stage extraction implemented traditionally (as shown in FIG. 6B), which resulted in additional product losses). See id. The residence time in the reactor is 1 hour. This single-phase reaction can be carried out in a dead-end flow configuration of a porous ceramic membrane disk-based reactor operating as a plug flow reactor (see, e.g., reactor of FIG. 5). Rather than using a gas mixture (See, e.g., Motamedhashemi, Y. et al., Flow-through catalytic membrane reactors for the destruction of a chemical warfare simulant: Dynamic performance aspects, Catalysis Today, 268, 130-141(2016)), a liquid mixture is used.

The solvent extraction process discussed herein includes three stages (shown in FIGS. 6B and 6C), each with a mixing tank for rapid mass transfer between layers and a static gravity decanter for layer separation, and provide the required purification with minimal product loss. Hydrazine is controlled to <2 parts per million (relative to 8 traditionally), and the deprotected impurity can be removed from as much as 5% traditionally to less than 1% of the total integrated product distribution detected by high-performance liquid chromatography (HPLC area %) after extraction.

Traditionally, DMSO was added to the product in a solution containing toluene, methanol, water and THF after membrane solvent extraction. Next, a rotary evaporator concentration method is used to remove the volatile solvents to yield a solution of 8 in DMSO (as shown in FIG. 6B). See id. In some embodiments, this process can be performed continuously using a perfluoropolymer CMS-3 based pervaporation membrane, which is highly selective in removing these solvents by employing a vacuum on the permeate side of the membrane and has very low permeation of DMSO vis-à-vis the other solvents. (See, e.g., J. Tang et al., Permeation and Sorption of Organic Solvents and Separation of their Mixtures through Amorphous Perfluoropolymer Membrane in Pervaporation, J. Membrane Sci., 447, 345-354 (2013); J. Tang et al., Perfluoropolymer Membrane behaves like a Zeolite Membrane in Dehydration of Aprotic Solvents, J. Membrane Sci., 421-422, 211-216 (2012)). This would provide a convenient membrane process where the CMS-3 membrane is completely inert and has extremely low permeation of DMSO. (See, e.g., J. Tang et al., Perfluoropolymer Membrane behaves like a Zeolite Membrane in Dehydration of Aprotic Solvents, J. Membrane Sci., 421-422, 211-216 (2012)).

Figure 6C:
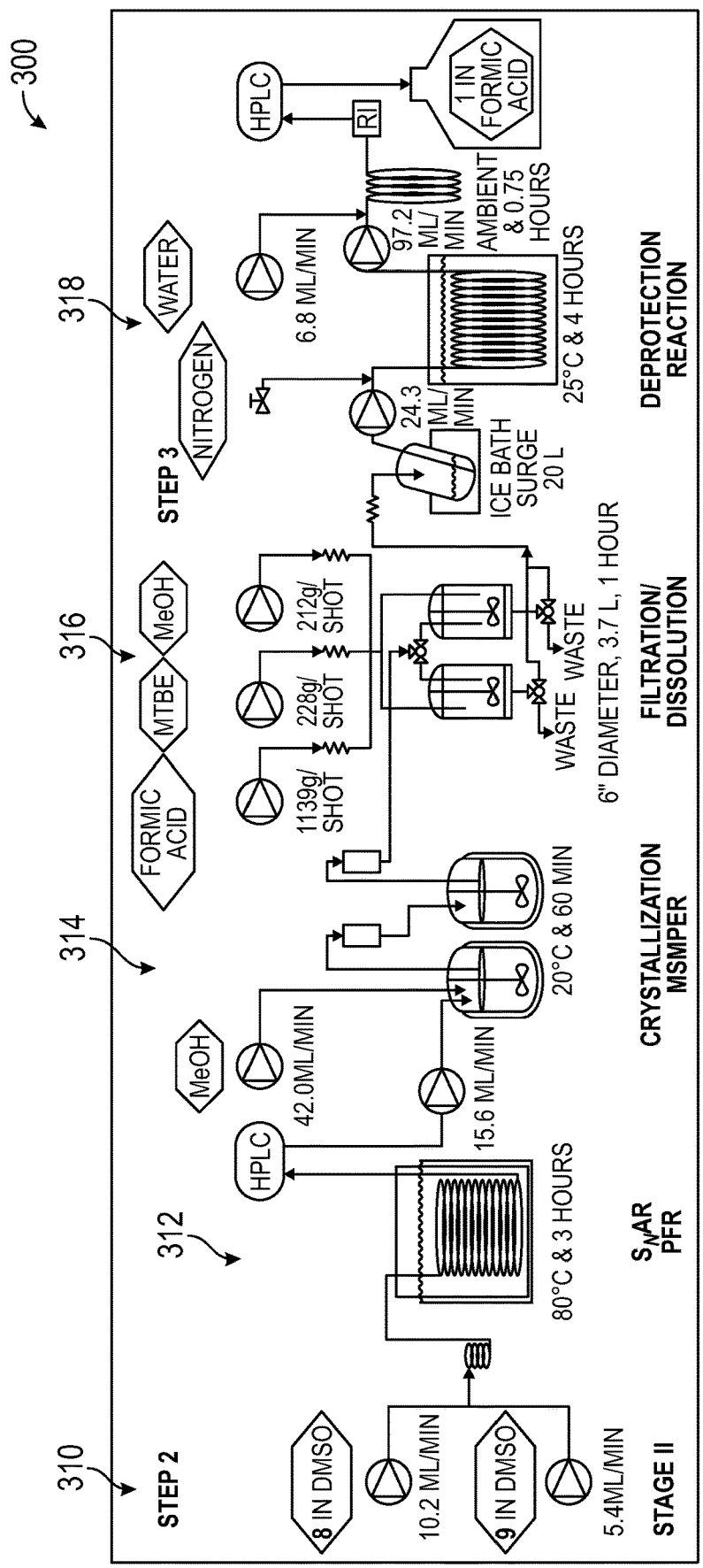

FIG. 6C shows a schematic of Stage II of the synthesis process 300. (See, e.g., Cole, K. P. et al., Kilogram-scale prexasertib monolactate monohydrate synthesis under continuous-flow CGMP conditions, Science, 356, 6281, 1144-1150 (2017)). Stage II includes an input 310 as step 2, an $S_N$Ar PFR section 312, an antisolvent crystallization MSMPR section 314, a filtration/dissolution section 316, and a deprotection reaction section 318. In Stage II, a solution of 8 in DMSO is mixed efficiently with a solution of pyrazine type compound 9 (N-ethyl morpholine) in DMSO in a porous hollow fiber membrane mixer before introduction into a ceramic membrane reactor of the type shown in FIG. 5 and maintained at 85° C. This allows a long residence time needed for the S N Ar type reaction between 8 and 9 to yield the pyrazole type compound 10. To remove residual 9, the pyrazole-arylated regioisomers, low levels of other process impurities, NEM-HCl, and DMSO, an antisolvent crystallization (FIG. 6B) can be implemented easily with methanol using the technique of porous hollow fiber anti-solvent crystallization (instead of using a mixed suspension mixed product removal (MSMPR) crystallizer as shown in FIG. 6C). (See, e.g., Chen, D. et al., Continuous synthesis of polymer-coated drug particles by a porous hollow fiber membrane-based antisolvent crystallization, Langmuir, 31, 432-441 (2015)). Membrane-based devices can replace every single conventional device used in synthesis of organic compounds to produce APIs in pharmaceutical industry. The process shown in FIGS. 6B-6C can therefore incorporate membrane-based devices for each of the devices used, leading to the compound 1 in FIG. 6C.

Next filtration and dissolution of 10 in formic acid (obtained after filtration and dissolution) and deprotection reaction is carried out in a reactor shown in FIG. 5 to end up with product 1 in formic acid. The reactor used is similar to that in FIG. 5, with the flow rate controlled to a very low rate to provide the needed liquid residence time of around 4 hours and an appropriate length of the membrane reactor. However, it can be useful to have a vertically upward configuration of the reactor such that any gasses evolving can naturally travel out through the top.

Figure 6D:
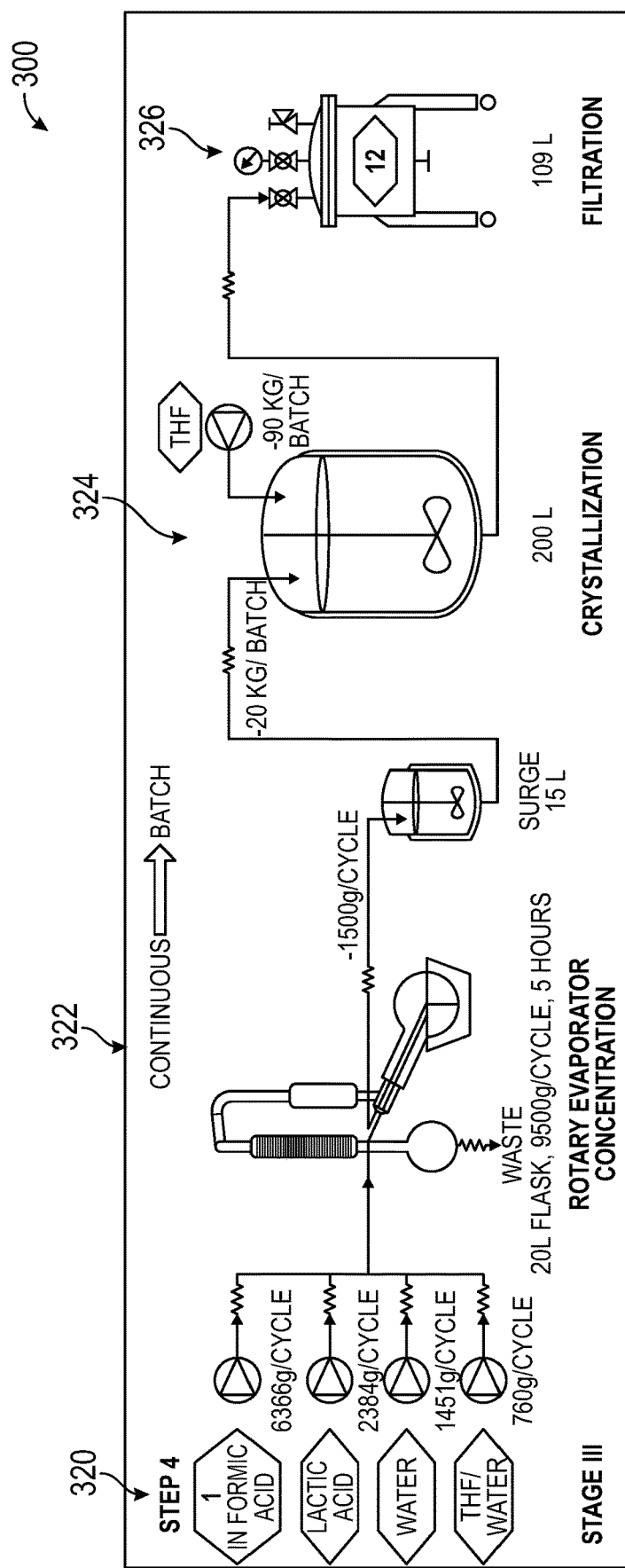

FIG. 6D is a schematic of Stage III synthesis process 300 of the system. (See, e.g., Cole, K. P. et al., Kilogram-scale prexasertib monolactate monohydrate synthesis under continuous-flow CGMP conditions, Science, 356, 6281, 1144-1150 (2017)). Stage III includes an input 320 at step 4, a rotary evaporator concentration section 322, a crystallization section 324, and a filtration section 326.

FIGS. 6B-6D illustrate how a traditional continuous manufacturing process of specific APIs can be modified such that API synthesis is performed using membrane-based devices and processes to replace conventional non-membrane devices and processes for synthesis of a particular API. In some embodiments, in Stage III illustrated in FIG. 6D, first the four solutions (i.e., 1 in formic acid, lactic acid, water and THF/water) may be mixed together in a porous hollow fiber membrane mixer and then introduced into a membrane evaporator-concentrator (a pervaporation membrane device) containing a perfluorocopolymer membrane to remove THF, water and formic acid with lactic acid remaining. The lactic acid salt is then crystallized using THF as an anti-solvent in a porous hollow fiber antisolvent crystallizer mentioned earlier. Here, replacement of a filtration device (last device in FIG. 6D) by a membrane device is not necessary since a filter is a membrane device.

Figure 7:
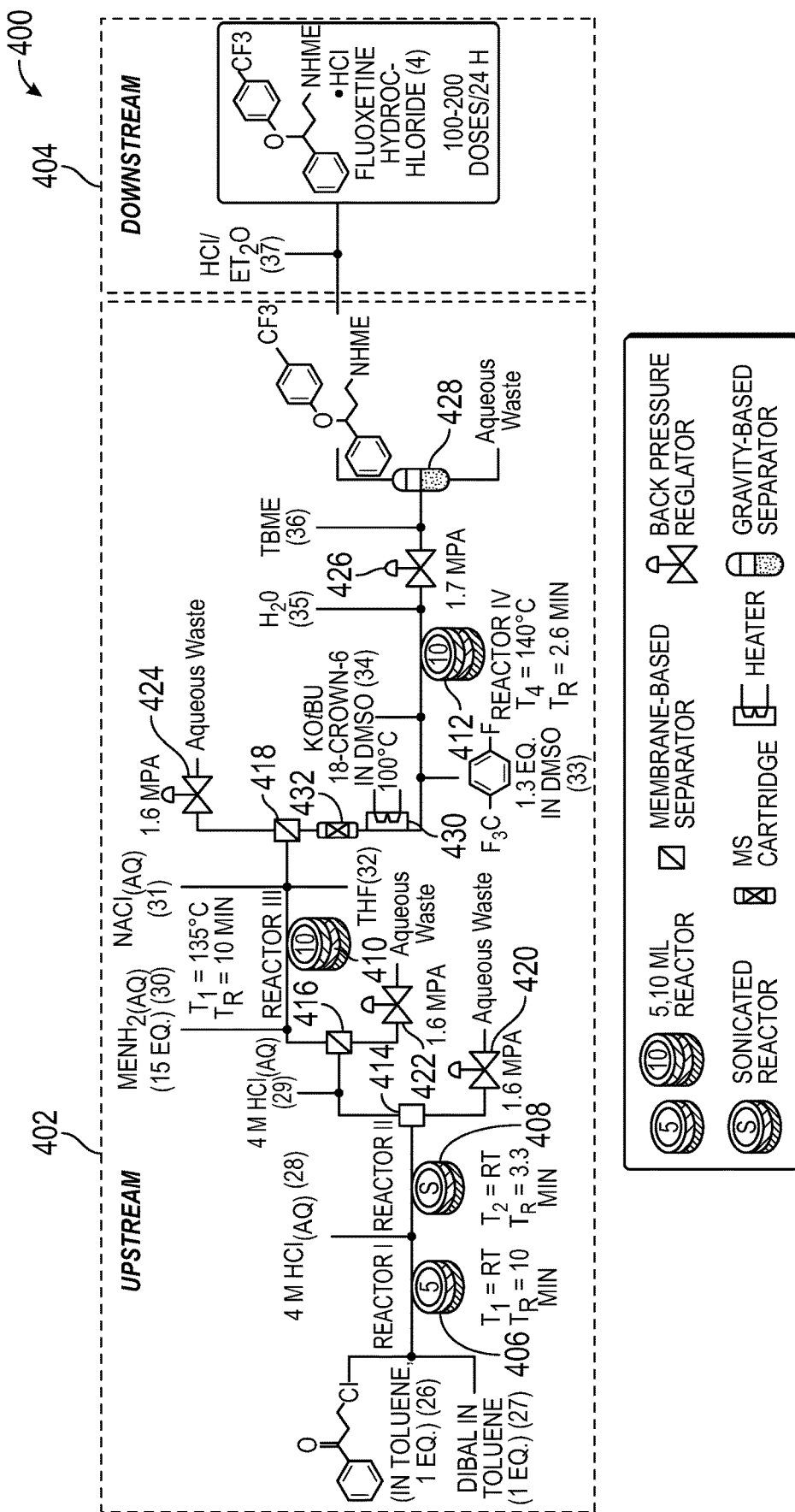
FIG. 7 is a schematic illustration of synthesis system for continuous manufacturing of fluoxetine hydrochloride (PROZAC®)

Another example of manufacturing a specific API using the exemplary system is the continuous manufacturing-based synthesis of fluoxetine hydrochloride (PROZAC®). (See, e.g., Adamo, A. et al., On-demand continuous-flow production of pharmaceuticals in a compact, reconfigurable system, Science, 352, 6281, 61-67 (2016), the entire contents of which are hereby incorporated herein by reference). FIG. 7 is a schematic of synthesis of the system 400 for continuous manufacturing of fluoxetine hydrochloride (PROZAC®). The system 400 includes an upstream section 402 and a downstream section 404. The upstream section 402 includes reactors 406, 408, 410, 412, membrane-based separators 414, 416, 418, back pressure regulators 420, 422, 424, 426, gravity based separator 428, heater 430, and MS cartridge 432. FIG. 7 therefore shows a flowchart detailing the upstream and downstream synthesis of fluoxetine hydrochloride.

In some embodiments, the first reactor 406 can be a membrane-based reactor, which is used to carry out diisobutylaluminum hydride (DIBAL) reduction of 3-Chloropropiophenone in toluene using a PFTR. In further embodiments, the membrane-based reactor may be the reactor of FIG. 5.

In some embodiments, the second reactor 408 may be a membrane-based reactor, e.g., a liquid-liquid (L-L) nondispersive membrane reactor (MR). A solution of 4M HCl can be added into a membrane reactor 408, e.g., a liquid-liquid (L-L) nondispersive membrane reactor (MR). The exiting stream from reactor 406 is introduced into the other side of the MR removing the need for a membrane separator. The aqueous stream goes to waste at the end of this reactor. Here, the L-L membrane reactor acts as a nondispersive membrane solvent extraction (MSX) device, which is used for solvent extraction in the membrane-based operations of the present disclosure, replacing traditional chemical engineering devices. The organic stream passes into an MSX device where 4M HCl stream is introduced into the aqueous side. The aqueous stream is withdrawn to waste at the end of this device as shown in FIG. 7.

In some embodiments, the third reactor 410 may be a membrane-based reactor, e.g., a L-L nondispersive extractor/reactor. When two immiscible liquid phases exist in an L-L reactor, there will be extraction occurring from one phase to the other phase. To the organic stream containing the intermediate alcohol entering the reactor 410 (Reactor III operating at 135° C.) which is a L-L nondispersive extractor/reactor, an aqueous methylamine solution is introduced to the aqueous side.

In some embodiments, the system 400 may include an additional membrane-based device, e.g., a L-L nondispersive membrane solvent extraction (MSX) device. The two immiscible product streams exiting reactor 410 can enter the additional membrane-based device, e.g., L-L nondispersive membrane solvent extraction (MSX) device, into which two streams are added: an aqueous 20% NaCl solution, and pure THF. The system 400 allows amino alcohol to go into a suitable organic solvent (THF) for further reaction downstream in Reactor IV (reactor 412). Before that reaction in reactor 412, the aqueous phase is taken out from the aqueous stream at the end of the MSX device and sent to waste. The water left in the organic phase stream is removed by passing the organic stream through a membrane pervaporation device using perfluoropolymer membrane discussed herein instead of sending it through a bed of zeolites (FIG. 7) (which is not a continuous process). (See, e.g., J. Tang et al., Perfluoropolymer membrane behaves like a zeolite membrane in dehydration of aprotic solvents, J. Membrane Sci., 421-422, 211-216 (2012); see also J. Tang et al., Permeation and sorption of organic solvents and separation of their mixtures through amorphous perfluoropolymer membrane in pervaporation, J. Membrane Sci., 447, 345-354 (2013)).

The dried organic stream is mixed with two DMSO solutions and enters reactor 412. In some embodiments, the reactor 412 may be a membrane-based reactor, e.g., the PFTR of FIG. 5. To the organic solution exiting reactor 412, successive streams of water and tert-butyl methyl ether (TBME) are added to the corresponding phase in a L-L MSX device to dispense with the subsequent gravity-based phase separator. The organic phase has the product as a crude solution of fluoxetine in TBME. Thus, virtually all of the steps implemented by traditional devices used in the system 400 of FIG. 7 can be performed in an improved manner with improved results using membrane-based devices, and such membrane-based devices can reduce the overall number of devices used by the system 400.

FIG. 8 is a schematic of membrane-facilitated continuous manufacturing operation or process 500 for Prexasertib Monolactate Monohydrate. In FIG. 8, F&D represents filtration and dissolution, HEX represents heat exchanger, L-L represents liquid-liquid, MEC represents membrane evaporator-concentrator, MM represents membrane mixer, MR represents membrane reactor, MSX represents membrane solvent extraction, PHFAC represents polymeric hollow fiber antisolvent crystallizer, and PV represents pervaporation. FIG. 8 illustrates the concept that many continuous API manufacturing processes based on traditional nonmembrane-based equipment/processes can be efficiently and effectively replaced by membrane-based equipment. Further, the number of equipment needed and (sometimes) the number of steps can be significantly reduced by using membrane-based equipment. FIG. 8 essentially shows the processes depicted in FIGS. 6B, 6C and 6D can be carried out by the membrane-based devices illustrated in FIG. 8.

Figure 9:
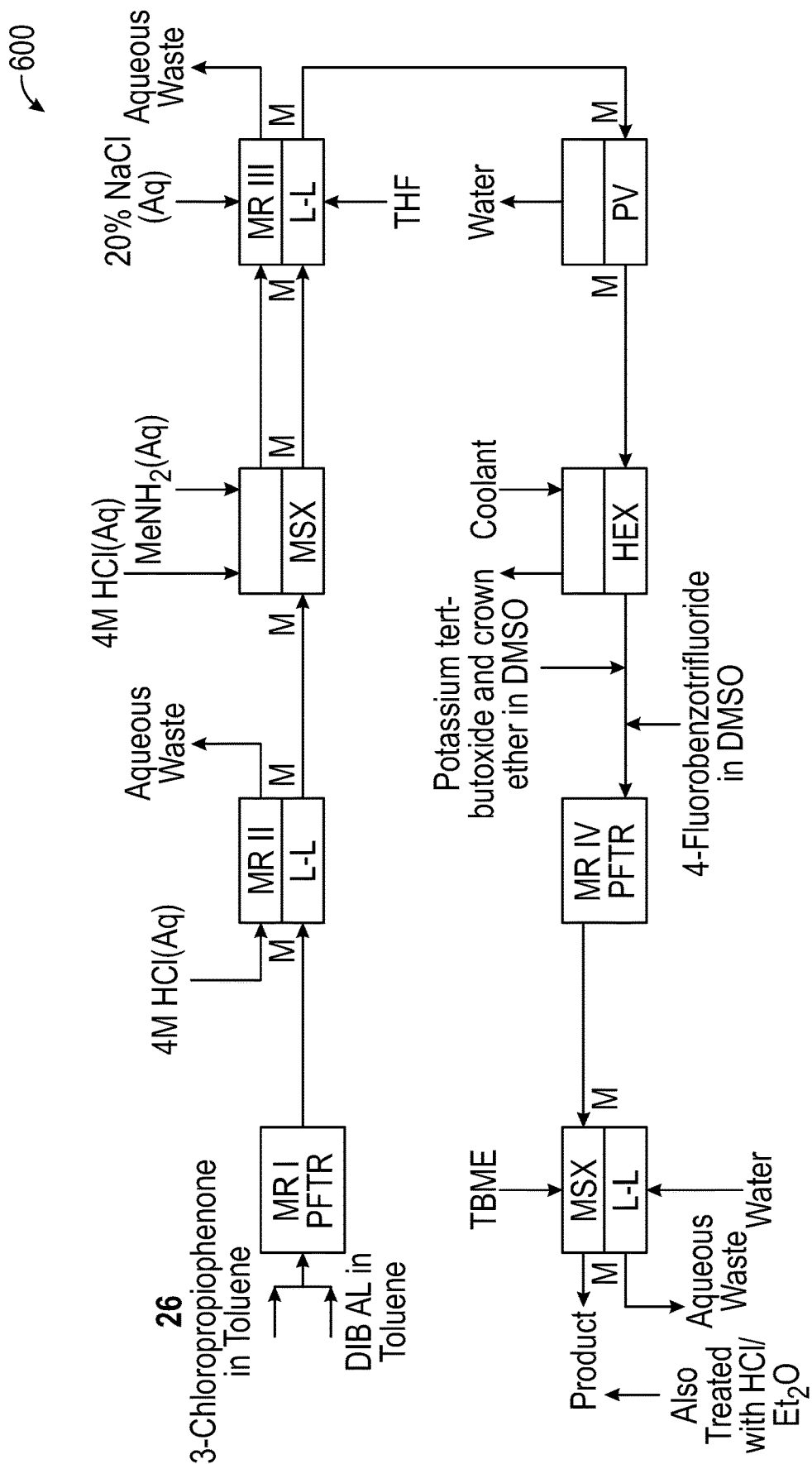
FIG. 9 is a schematic of continuous membrane-facilitated synthesis of fluoxetine hydrochloride (PROZAC®)
Figure 10:
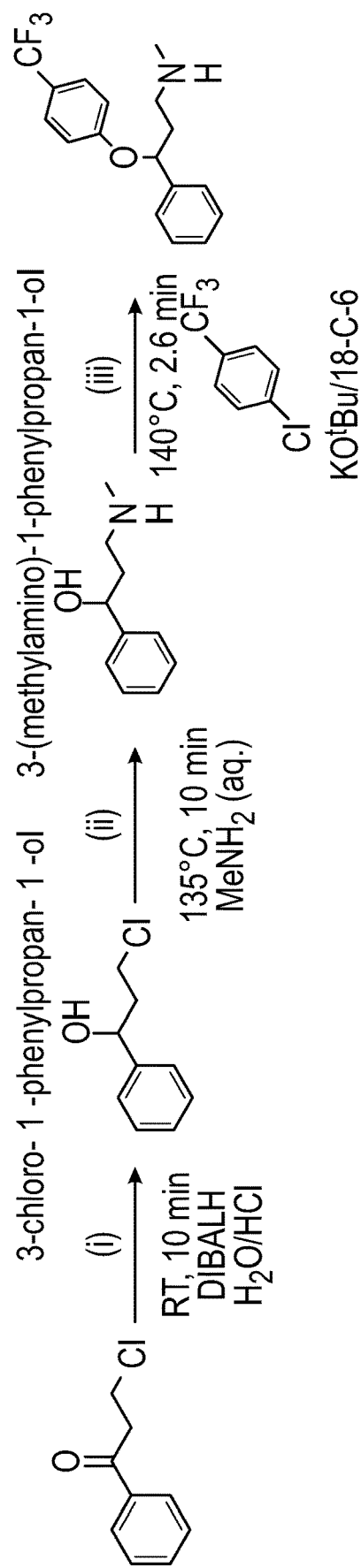
FIG. 10 is a schematic of a continuous membrane-facilitated synthetic route for synthesis of fluoxetine hydrochloride.

FIG. 9 is a schematic of continuous membrane-facilitated synthesis process 600 of fluoxetine hydrochloride (PROZAC®), and FIG. 10 is a schematic of a continuous membrane-facilitated synthetic route for synthesis of fluoxetine hydrochloride. In FIG. 9, DMSO represents dimethyl sulfoxide, HEX represents heat exchanger, L-L represents liquid-liquid, MeNH$_2$ represents methylamine, MR represents membrane reactor, PFTR represents pore flow through reactor, MSX represents membrane solvent extraction, PV represents pervaporation, and TBME represents tert-butyl methyl ether. FIG. 9 reinforces the idea proposed herein, i.e., that many continuous API manufacturing processes based on traditional nonmembrane-based equipment/processes can be efficiently and effectively replaced by membrane-based equipment. The continuous manufacturing example of PROZAC™ shown in FIG. 7 using traditional manufacturing devices can be replaced conveniently by membrane-based devices and processes. Further, the number of equipment needed and (sometimes) the number of steps can be significantly reduced by use of membrane-based equipment.

Thus, the exemplary synthesis systems discussed herein incorporate a membrane device into every or virtually every unit used in API manufacturing process. All units in the system are connected in a serial fashion and operate continuously such that continuous membrane-based production of APIs is achieved. There is no batch processing in the system. In general, the heart of any API production system consists of the reactors for synthesis of intermediates and finally the API. Typically, quite a few reaction steps are involved in traditional API synthesis anywhere from 2, 3, 4 to around 20 reaction steps (or more). The systems discussed herein ensure that each reaction step can be carried out in a membrane reactor in a continuous fashion. Steps related to any reaction carried out before introduction to the reactor (such as mixing reactants, heating the feed) or after the reaction (such as quenching or cooling) can be carried out using membrane-based devices. In some embodiments, the membrane reactor itself can carry out such functions. After each reaction, membrane separation steps can be coupled with the membrane reactor output and separations/purifications of the intermediates/API can be carried out. Use of such system can provide for extraordinary enhancements in reactions in a multistep API synthesis and production process employing membrane reactors at every synthesis step which are then supported by membrane separations at each post-reaction processing step. All of these steps can be carried out continuously to continuously manufacture APIs.

Thus, a membrane-based production process is provided to produce active pharmaceutical ingredients (APIs). Virtually every step in a continuous multi-step synthesis-based process to produce an API in the pharmaceutical industry can be carried out with a membrane unit instead of a conventional non-membrane unit. Membrane reactors can achieve a synthesis level not achievable by conventional tubular reactors. Membrane solvent extraction can allow nondispersive solvent extraction with great efficiency. Membrane pervaporation can be used to selectively remove volatile solvents from a mixture. Organic solvent nanofiltration and organic solvent reverse osmosis can remove solvents and hold back reaction intermediates or the API at room temperature. Membrane crystallizers, membrane mixers, solid hollow fiber, and ceramic tubular exchangers can now carry out the processes of crystallization, mixing and heat exchange respectively much more efficiently than conventional non-membrane based devices. For continuous multistep manufacturing of active pharmaceutical ingredients (APIs) in the molecular weight range of ~150-1000 Da, incorporation of such membrane devices at every step of the API manufacturing process can overcome many deficiencies of batch manufacturing of pharmaceuticals as well as those of continuous processes using non-membrane devices and processes.

While exemplary embodiments have been described herein, it is expressly noted that these embodiments should not be construed as limiting, but rather that additions and modifications to what is expressly described herein also are included within the scope of the invention. Moreover, it is to be understood that the features of the various embodiments described herein are not mutually exclusive and can exist in various combinations and permutations, even if such combinations or permutations are not made express herein, without departing from the spirit and scope of the invention.

The invention claimed is:

1. A method for continuous manufacturing of prexasertib monolactate monohydrate, said method comprising the steps of:
   (a) combining compound 7 with hydrazine in the presence of acetic acid in methanol and THF at the temperature of about 130° C. to produce compound 8:

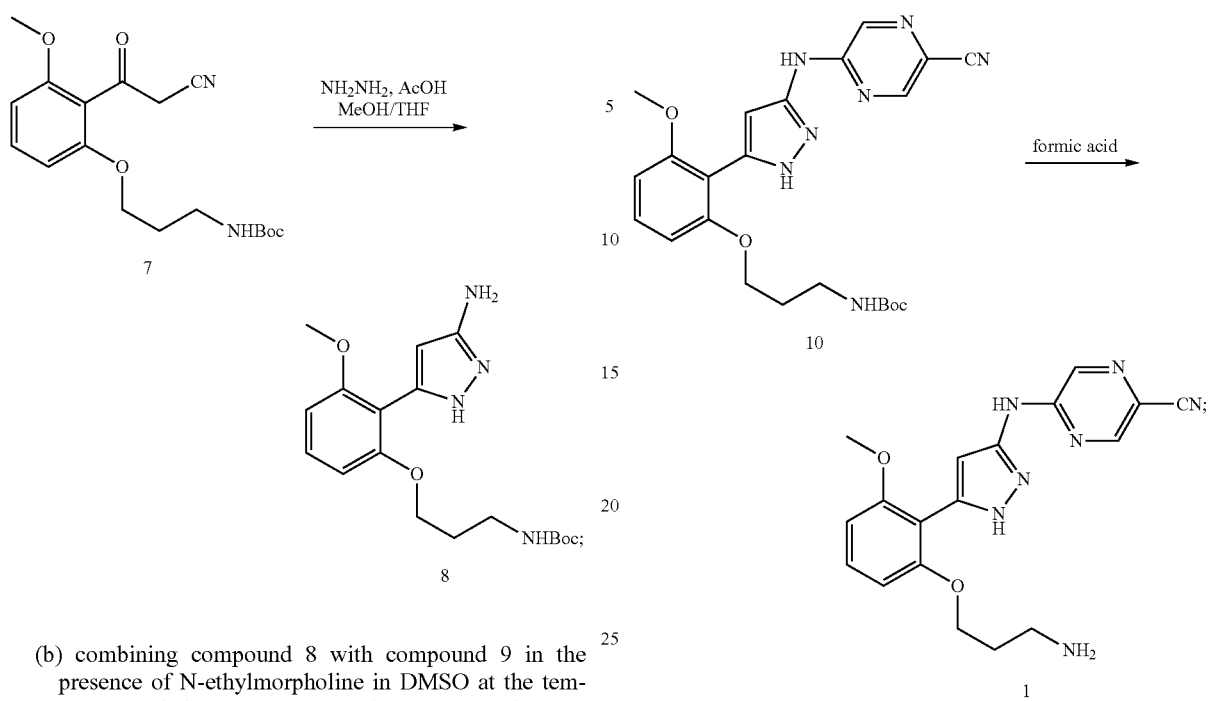

(b) combining compound 8 with compound 9 in the presence of N-ethylmorpholine in DMSO at the temperature of about 85° C. to produce compound 10:

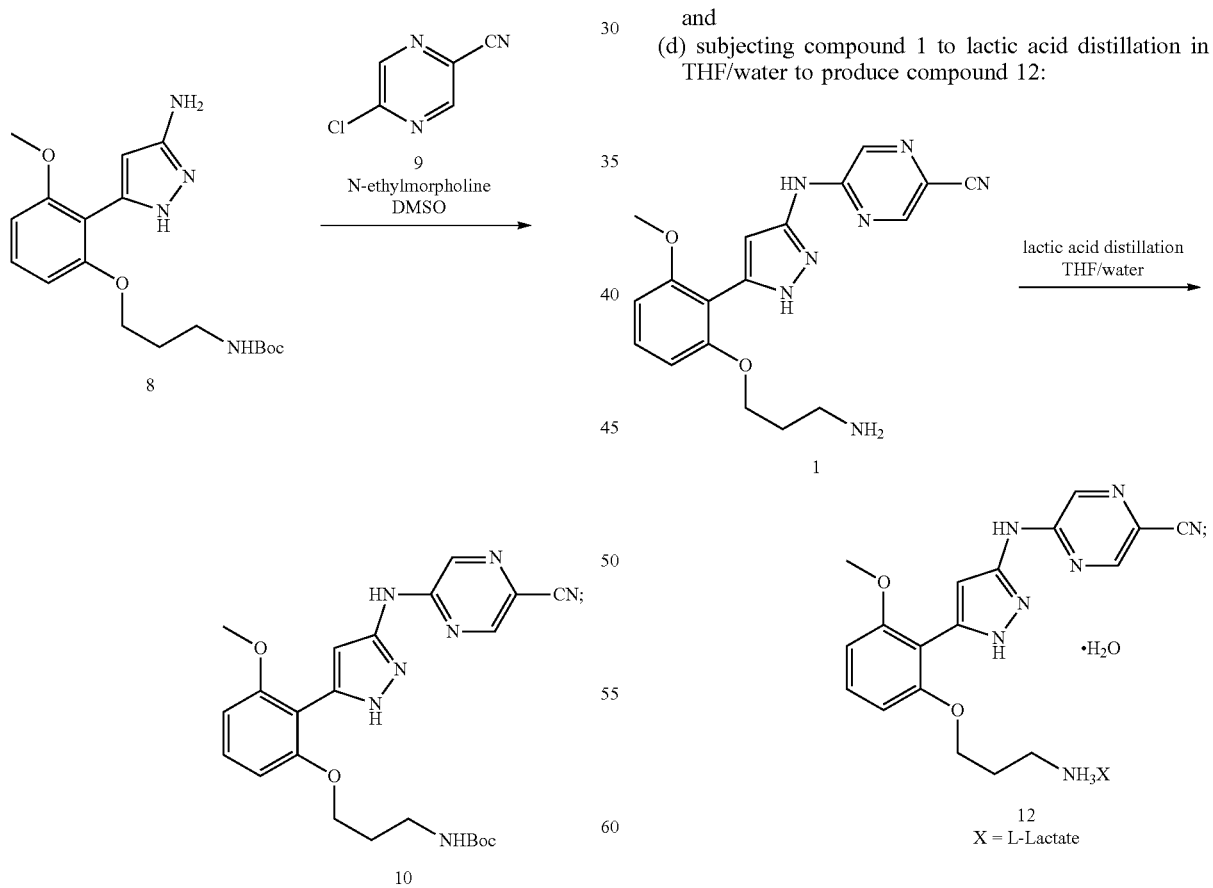

(c) deprotecting compound 10 by combining it with formic acid at the temperature of about 25° to produce compound 1:

and (d) subjecting compound 1 to lactic acid distillation in THF/water to produce compound 12:

wherein each of steps (a)-(d) is carried out in a series of units connected to each other to support continuous flow; and wherein said series of units comprises at least one membrane-based unit, wherein after step (a), combining compound 8 with toluene and carrying out countercurrent solvent extraction using the membrane-based unit to yield compound 8 in a mixture of toluene, methanol, water and THF, wherein the membrane-based unit is a pervaporation membrane device.

2. The method of claim 1, wherein at least step (a) is carried out in a membrane-based unit.

3. The method of claim 1, wherein at least step (b) is carried out in a membrane-based unit.

4. The method of claim 1, wherein at least step (c) is carried out in a membrane-based unit.

5. The method of claim 1, wherein at least step (d) is carried out in a membrane-based unit.

6. The method of claim 2, wherein said membrane-based unit is a membrane-based reactor unit, which is Pore Flow Through Reactor (PFTR).

7. The method of claim 1, further comprising
adding DMSO to compound 8 in toluene, methanol, water and THF to produce a mixture; and
introducing said mixture into a membrane-based unit to remove toluene, methanol and water from said mixture by pervaporation.

8. The method of claim 7, wherein said membrane-based unit comprises a perfluorocopolymer membrane.

9. The method of claim 1, comprising, prior to step (b), combining compound 8 with compound 9 in DMSO in a membrane-based unit to produce a mixture of compound 8 and compound 9 in DMSO, wherein said membrane-based unit is a membrane mixer.

10. The method of claim 9, wherein said membrane mixer is a porous hollow membrane mixer.

11. The method of claim 9, wherein said membrane-based unit is a Pore Flow Through Reactor (PFTR).

12. The method of claim 1, wherein said membrane-based unit is a Pore Flow Through Reactor (PFTR).

13. The method of claim 1, wherein said membrane-based unit is a pervaporation membrane device.

14. The method of claim 13, wherein said pervaporation membrane device comprises a perfluorocopolymer membrane.

15. A system for continuous manufacturing of prexasertib monolactate monohydrate in accordance with the method of claim 1, said system comprising a series of units connected to each other to support continuous flow, wherein at least one unit in said system is a membrane-based unit.

* * * * *